United States Patent
Peterman et al.

(10) Patent No.: US 7,988,734 B2
(45) Date of Patent: *Aug. 2, 2011

(54) SPINAL SYSTEM AND METHOD INCLUDING LATERAL APPROACH

(75) Inventors: Marc M. Peterman, Memphis, TN (US); Frank Bono, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/800,145

(22) Filed: May 10, 2010

(65) Prior Publication Data

US 2010/0262249 A1    Oct. 14, 2010

Related U.S. Application Data

(63) Continuation of application No. 11/091,738, filed on Mar. 28, 2005, now Pat. No. 7,749,269.

(51) Int. Cl.
*A61F 2/44* (2006.01)
(52) U.S. Cl. .................... 623/17.11; 623/17.16
(58) Field of Classification Search ............ 623/17.11, 623/17.16; 606/90, 99
See application file for complete search history.

(56) References Cited

U.S. PATENT DOCUMENTS

| | | | |
|---|---|---|---|
| 4,545,374 A | 10/1985 | Jacobson | |
| 5,306,308 A | 4/1994 | Gross et al. | |
| 5,534,028 A | 7/1996 | Bao et al. | |
| 5,792,044 A | 8/1998 | Foley et al. | |
| 6,059,829 A | 5/2000 | Schlapfer et al. | |
| 6,258,125 B1 | 7/2001 | Paul et al. | |
| 6,290,724 B1 | 9/2001 | Marino | |
| 6,368,325 B1 | 4/2002 | McKinley et al. | |
| 6,371,986 B1 | 4/2002 | Bagby | |
| 6,387,130 B1 | 5/2002 | Stone et al. | |
| 6,428,544 B1 | 8/2002 | Ralph et al. | |
| 6,436,102 B1 | 8/2002 | Ralph et al. | |
| 6,443,987 B1 | 9/2002 | Bryan | |
| 6,447,548 B1 | 9/2002 | Ralph et al. | |
| 6,471,725 B1 | 10/2002 | Ralph et al. | |
| 6,478,801 B1 | 11/2002 | Ralph et al. | |
| 6,482,233 B1 * | 11/2002 | Aebi et al. | 623/17.11 |
| 6,485,518 B1 | 11/2002 | Cornwall et al. | |
| 6,500,206 B1 | 12/2002 | Bryan | |
| 6,524,320 B2 | 2/2003 | DiPoto | |
| 6,554,864 B2 | 4/2003 | Ralph et al. | |
| 6,562,047 B2 | 5/2003 | Ralph et al. | |
| 6,607,559 B2 | 8/2003 | Ralph et al. | |
| 6,610,089 B1 | 8/2003 | Liu et al. | |

(Continued)

FOREIGN PATENT DOCUMENTS

EP    1259175 B1    7/2004

(Continued)

OTHER PUBLICATIONS

Maxcess XLIF 90 Surgical Technique, Copyright 2003 NuVasive, Inc., 27 pages, San Diego, California.

*Primary Examiner* — Eduardo C Robert
*Assistant Examiner* — Ellen C Hammond

(57) ABSTRACT

Embodiments of the invention include devices and methods for implanting a vertebral body spacer. A lateral surgical approach is contemplated with some disclosed procedures. Instruments of some embodiments are insertable into a disc space to achieve distraction, to determine a desired disc space height, and to select a corresponding implant.

20 Claims, 27 Drawing Sheets

U.S. PATENT DOCUMENTS

| | | |
|---|---|---|
| 6,613,090 B2 | 9/2003 | Eckhof et al. |
| 6,623,525 B2 | 9/2003 | Ralph et al. |
| 6,648,895 B2 | 11/2003 | Burkus et al. |
| 6,666,891 B2 | 12/2003 | Boehm, Jr. et al. |
| 6,692,434 B2 | 2/2004 | Ritland |
| 6,723,096 B1 * | 4/2004 | Dorchak et al. ............ 606/86 A |
| 6,740,119 B2 | 5/2004 | Ralph et al. |
| 6,743,234 B2 | 6/2004 | Burkus et al. |
| 6,805,716 B2 | 10/2004 | Ralph et al. |
| 6,837,904 B2 | 1/2005 | Ralph et al. |
| 6,843,804 B2 | 1/2005 | Bryan |
| 6,855,151 B2 | 2/2005 | Ralph et al. |
| 7,063,725 B2 * | 6/2006 | Foley .......................... 623/17.16 |
| 7,125,425 B2 * | 10/2006 | Foley et al. ................. 623/17.16 |
| 7,192,447 B2 * | 3/2007 | Rhoda ......................... 623/17.11 |
| 7,311,734 B2 | 12/2007 | Van Hoeck et al. |
| 7,857,852 B2 * | 12/2010 | Kuras ......................... 623/17.11 |
| 2001/0016741 A1 | 8/2001 | Burkus et al. |
| 2002/0068936 A1 | 6/2002 | Burkus et al. |
| 2002/0138147 A1 | 9/2002 | Cohen |
| 2002/0165612 A1 | 11/2002 | Gerber et al. |
| 2003/0014057 A1 | 1/2003 | Ralph et al. |
| 2003/0014109 A1 | 1/2003 | Ralph et al. |
| 2003/0014110 A1 | 1/2003 | Ralph et al. |
| 2003/0014113 A1 | 1/2003 | Ralph et al. |
| 2003/0014114 A1 | 1/2003 | Ralph et al. |
| 2003/0014115 A1 | 1/2003 | Ralph et al. |
| 2003/0014116 A1 | 1/2003 | Ralph et al. |
| 2003/0023245 A1 | 1/2003 | Ralph et al. |
| 2003/0023309 A1 | 1/2003 | Ralph et al. |
| 2003/0023310 A1 | 1/2003 | Ralph et al. |
| 2003/0028196 A1 | 2/2003 | Bonutti |
| 2003/0028252 A1 | 2/2003 | Ralph et al. |
| 2003/0032962 A1 * | 2/2003 | McGahan et al. ............... 606/80 |
| 2003/0130737 A1 | 7/2003 | McGahan et al. |
| 2003/0139814 A1 | 7/2003 | Bryan |
| 2003/0153975 A1 * | 8/2003 | Byrd et al. ................. 623/17.11 |
| 2003/0195627 A1 | 10/2003 | Ralph et al. |
| 2004/0002711 A1 | 1/2004 | Berry |
| 2004/0010259 A1 | 1/2004 | Keller et al. |
| 2004/0024406 A1 | 2/2004 | Ralph et al. |
| 2004/0024407 A1 | 2/2004 | Ralph et al. |
| 2004/0024408 A1 | 2/2004 | Burkus et al. |
| 2004/0082999 A1 * | 4/2004 | Mathys et al. ............. 623/17.11 |
| 2004/0093089 A1 | 5/2004 | Ralph et al. |
| 2004/0127990 A1 | 7/2004 | Bartish |
| 2004/0127994 A1 * | 7/2004 | Kast et al. .................. 623/17.16 |
| 2004/0138534 A1 | 7/2004 | Ritland |
| 2004/0158326 A1 | 8/2004 | Ralph et al. |
| 2004/0162616 A1 * | 8/2004 | Simonton et al. .......... 623/17.11 |
| 2004/0176665 A1 | 9/2004 | Branch et al. |
| 2004/0176775 A1 | 9/2004 | Burkus et al. |
| 2004/0199168 A1 | 10/2004 | Bertagnoli et al. |
| 2004/0230100 A1 | 11/2004 | Shluzas |
| 2004/0236370 A1 | 11/2004 | Ralph et al. |
| 2005/0010234 A1 | 1/2005 | Ralph et al. |
| 2005/0043802 A1 | 2/2005 | Eisermann et al. |
| 2005/0149035 A1 | 7/2005 | Pimenta et al. |
| 2006/0195114 A1 | 8/2006 | Bertagnoli |
| 2006/0217806 A1 | 9/2006 | Peterman et al. |

FOREIGN PATENT DOCUMENTS

| | | |
|---|---|---|
| EP | 1437105 A1 | 7/2004 |
| JP | 2004209249 | 7/2004 |
| WO | WO 99/37255 A1 | 7/1999 |
| WO | WO 00/44288 A1 | 8/2000 |
| WO | WO 01/62166 A2 | 8/2001 |
| WO | WO 01/62191 A2 | 8/2001 |
| WO | WO 01/80785 A1 | 11/2001 |
| WO | WO 01/95838 A1 | 12/2001 |
| WO | WO 02/058762 A2 | 8/2002 |
| WO | WO 02/062235 A2 | 8/2002 |
| WO | WO 02/076350 A1 | 10/2002 |
| WO | WO 03/005887 A2 | 1/2003 |
| WO | WO 03/026482 A2 | 4/2003 |
| WO | WO 03/026514 A1 | 4/2003 |
| WO | WO 03/037170 A2 | 5/2003 |
| WO | WO 2004/002332 A1 | 1/2004 |
| WO | WO 2004/064634 A1 | 8/2004 |
| WO | WO 2004/071359 A1 | 8/2004 |
| WO | WO 2004/093691 A2 | 11/2004 |
| WO | WO 2005/030318 A1 | 4/2005 |

* cited by examiner

SPINAL SYSTEM AND METHOD INCLUDING LATERAL APPROACH

CROSS-REFERENCE TO RELATED APPLICATIONS

The present application is a continuation of U.S. patent application Ser. No. 11/091,738 filed on Mar. 28, 2005 now U.S. Pat. No. 7,749,269, which is related to U.S. patent application Ser. No. 11/091,739 entitled "SPINAL DEVICE INCLUDING LATERAL APPROACH" and also filed on Mar. 28, 2005, the contents of each application hereby incorporated by reference in its entirety.

FIELD OF THE INVENTION

The present invention relates generally to the field of spinal implants, and more particularly relates to vertebral body spacers and methods of implanting vertebral body spacers.

BACKGROUND

Vertebral body spacers are used in response to degenerative disc disease or other spinal conditions to maintain a space between adjacent spinal vertebrae. Typically, the goal of an associated surgical procedure is for the adjacent vertebrae to grow or "fuse" together. A vertebral body spacer is usually made of a biocompatible synthetic material or allograft bone.

Vertebral body spacers have been implanted from anterior, transforaminal, oblique, posterior, and other surgical approaches for a number of years. A lateral surgical approach has also been accomplished. However, the prior implants, instruments, and methods associated with a lateral approach are not optimal.

Existing implants used with a lateral approach may fail to conform to the natural curvatures of vertebral endplates or to the natural anterior curves of the anterior portion of the vertebral body. Instruments and lateral implants are not necessarily suited to efficiently distract the disc space without damaging the adjacent endplates. The shapes of instruments and lateral implants are not particularly coordinated to reduce disruption to the surrounding tissues. Current methods may require significant cutting and manipulation of bone and other tissue.

The description herein of certain disadvantages and problems associated with known devices, apparatus, and methods is not intended to limit the scope of the invention to the exclusion of those known devices, apparatus, and methods. Embodiments of the invention may include some or all of the known devices, apparatus, and methods without suffering from the disadvantages and problems described herein.

Methods and devices for performing surgery are disclosed in U.S. Pat. No. 5,792,044, "Devices and Methods for Percutaneous Surgery," filed Mar. 22, 1996; U.S. patent application Ser. No. 10/274,856, "Systems and Techniques for Restoring and Maintaining Intervertebral Anatomy," filed Oct. 21, 2002; U.S. patent application Ser. No. 10/766,167, "Systems and Techniques for Restoring and Maintaining Intervertebral Anatomy," filed Jan. 28, 2004; and U.S. patent application Ser. No. 10/792,358, "Instruments and Methods for Minimally Invasive Tissue Retraction and Surgery," filed Mar. 3, 2004, all of which are incorporated by reference herein. Any of the relevant implants, instruments, methods, or surgical approaches described in the incorporated references that are adaptable for use with components of the present invention and are within the scope of the invention described and claimed herein.

SUMMARY

One embodiment of the invention is an implant with an elongated body positionable in a spinal disc space. The embodiment has a convexly curved upper surface orientable toward an endplate of an upper vertebra, a convexly curved lower surface orientable toward an endplate of a lower vertebra, a leading end portion, and an opposite trailing end portion. An at least partially convexly curved anterior sidewall extends between the leading end portion and the trailing end portion, and a posterior sidewall extends between the leading end portion and the trailing end portion. The body includes a height between the upper and lower surfaces corresponding to a desired disc space height between the upper vertebra endplate and the lower vertebra endplate. The leading end portion is structured for insertion into the disc space in an at least partially collapsed condition and the height is sized to restore the collapsed disc space to the desired disc space height as the body is inserted in the collapsed disc space.

An embodiment of the invention is an implant with an elongated body positionable in a spinal disc space. The embodiment has an upper surface orientable toward an endplate of an upper vertebra, a lower surface orientable toward an endplate of a lower vertebra, a leading end portion, and an opposite trailing end portion. An at least partially convexly curved anterior sidewall extends between the leading end portion and the trailing end portion, and a posterior sidewall extends between the leading end portion and the trailing end portion, the posterior sidewall having an average height less than the average height of the anterior sidewall. At least one of the upper surface and the lower surface are curved such that the height of the implant near its center is greater than the height of the implant at its leading end. The height of the implant near its center is between about 7 mm and 19 mm. The height of the implant at its leading end is at least about 3 mm less than the height of the implant near its center.

Another embodiment of the invention is an implant with an elongated body positionable in a spinal disc space. The embodiment has a convexly curved upper surface, a convexly curved lower surface, a leading end portion defined by a convexly curved surface that extends between the upper surface and the lower surface, and a trailing end portion defined by a substantially planar surface that extends between the upper surface and the lower surface. An anterior sidewall is defined by a maximally anterior portion, a first curved portion extending between the leading end portion and the maximally anterior portion, and a second curved portion extending between the trailing end portion and the maximally anterior portion. A posterior sidewall extends between the leading end portion and the trailing end portion. The height of the implant near its center is between about 8 mm and 14 mm. The height of the implant at its leading end is at least about 3 mm less than the height of the implant near its center.

An additional embodiment of the invention includes an implant with an elongated body positionable in a spinal disc space. The embodiment has an upper surface means orientable toward an endplate of an upper vertebra for substantially cooperatively fitting with the upper vertebra, a lower surface means orientable toward an endplate of a lower vertebra for substantially cooperatively fitting with the lower vertebra, and a leading end means for promoting insertion of the implant between the upper vertebra and the lower vertebra, and an opposite trailing end portion. The embodiment also has an at least partially convexly curved anterior sidewall means for enabling anterior placement of a portion of the implant between the cortical rim of the upper vertebra and the cortical rim of the lower vertebra. A posterior sidewall extends between the leading end means and the trailing end portion. The height of the implant near its center is between about 7 mm and 19 mm. The height of the implant at its leading end is at least about 3 mm less than the height of the implant near its center.

Yet another embodiment of the invention is a system for placing an implant between an endplate of an upper vertebra and an endplate of a lower vertebra. The embodiment includes a trial instrument set with at least two instruments of different sizes. Each trial instrument of the trial instrument set has an upper surface orientable toward the upper vertebra, a lower surface orientable toward the lower vertebra, and a leading end portion with segments that diverge from the leading end to meet the upper surface and the lower surface respectively. The embodiment also includes an implant with an elongated body positionable in a spinal disc space. The implant has an upper surface orientable toward the upper vertebra, a lower surface orientable toward the lower vertebra, a leading end portion and an opposite trailing end portion, an at least partially convexly curved anterior sidewall extending between the leading end portion and the trailing end portion, and a posterior sidewall extending between the leading end portion and the trailing end portion. At least one of the upper surface and the lower surface are curved such that the height of the implant near its center is greater than the height of the implant at its leading end, and the height of the implant near its center is between about 7 mm and 19 mm. The height of the implant at its leading end is at least about 3 mm less than the height of the implant near its center.

Still another embodiment of the invention is a method of surgically placing an implant between vertebral bodies from a generally lateral surgical approach. The embodiment includes positioning a patient such that an operative side of the patient is accessible, making an incision in the operative side of the patient between the ribcage and the iliac crest of the patient, locating an initial insertion dilator between the vertebral bodies, dilating tissue with a first concentric dilator that fits over the initial insertion dilator to further open the incision, removing vertebral disc material to create an opening for the implant between the vertebral bodies, inserting a trial instrument between the vertebral bodies, and inserting between the vertebral bodies an implant. The implant has an upper surface orientable toward the upper vertebra, a lower surface orientable toward the lower vertebra, a leading end portion and an opposite trailing end portion, an anterior sidewall extending between the leading end portion and the trailing end portion, and a posterior sidewall extending between the leading end portion and the trailing end portion. At least one of the upper surface and the lower surface are curved such that the height of the implant near its center is greater than the height of the implant at its leading end. The height of the implant near its center is between about 7 mm and 19 mm. The height of the implant at its leading end is at least about 3 mm less than the height of the implant near its center.

Another embodiment of the invention is a method of surgically placing an implant between vertebral bodies from a generally lateral surgical approach. The embodiment includes positioning a patient such that an operative side of the patient is accessible, making an incision in the operative side of the patient between the ribcage and the iliac crest of the patient, locating an initial insertion dilator between the vertebral bodies, dilating tissue with a first concentric dilator that fits over the initial insertion dilator to further open the incision, removing vertebral disc material to create an opening for the implant between the vertebral bodies, inserting a trial instrument between the vertebral bodies, and inserting between the vertebral bodies an implant. The implant has a convexly curved upper surface orientable toward an endplate of an upper vertebra, a convexly curved lower surface orientable toward an endplate of a lower vertebra, a leading end portion and an opposite trailing end portion, an anterior sidewall extending between the leading end portion and the trailing end portion, and a posterior sidewall extending between the leading end portion and the trailing end portion. The body includes a height between the upper and lower surfaces corresponding to a desired disc space height between the upper vertebra endplate and the lower vertebra endplate. The leading end portion is structured for insertion into the disc space in an at least partially collapsed condition and the height is sized to restore the collapsed disc space to the desired disc space height as the body is inserted in the collapsed disc space.

An embodiment of the invention is a method of surgically placing an implant between vertebral bodies from a generally lateral surgical approach. The embodiment includes making an incision in an operative side of a patient between the ribcage and the iliac crest of the patient, inserting a trial instrument between the vertebral bodies, and inserting between the vertebral bodies an implant with an elongated body. The implant has an upper surface orientable toward an endplate of an upper vertebra, a lower surface orientable toward an endplate of a lower vertebra, a leading end portion and an opposite trailing end portion, an anterior sidewall defined by a maximally anterior portion, a first curved portion extending between the leading end portion and the maximally anterior portion, and a second curved portion extending between the trailing end portion and the maximally anterior portion, and a posterior sidewall extending between the leading end portion and the trailing end portion. The act of inserting the implant includes placing the implant anteriorly between the vertebral bodies such that the first curved portion and the second curved portion of the anterior sidewall are substantially located between a cortical rim of the upper vertebra and a cortical rim of the lower vertebra.

BRIEF DESCRIPTION OF THE DRAWINGS

FIG. 13*b* is a side elevation view of the distal portion of the trial instrument of FIG. 13*a*.

FIG. 13c is an end elevation view of the distal portion of the trial instrument of FIG. 13a.

DETAILED DESCRIPTION

Figure 1:
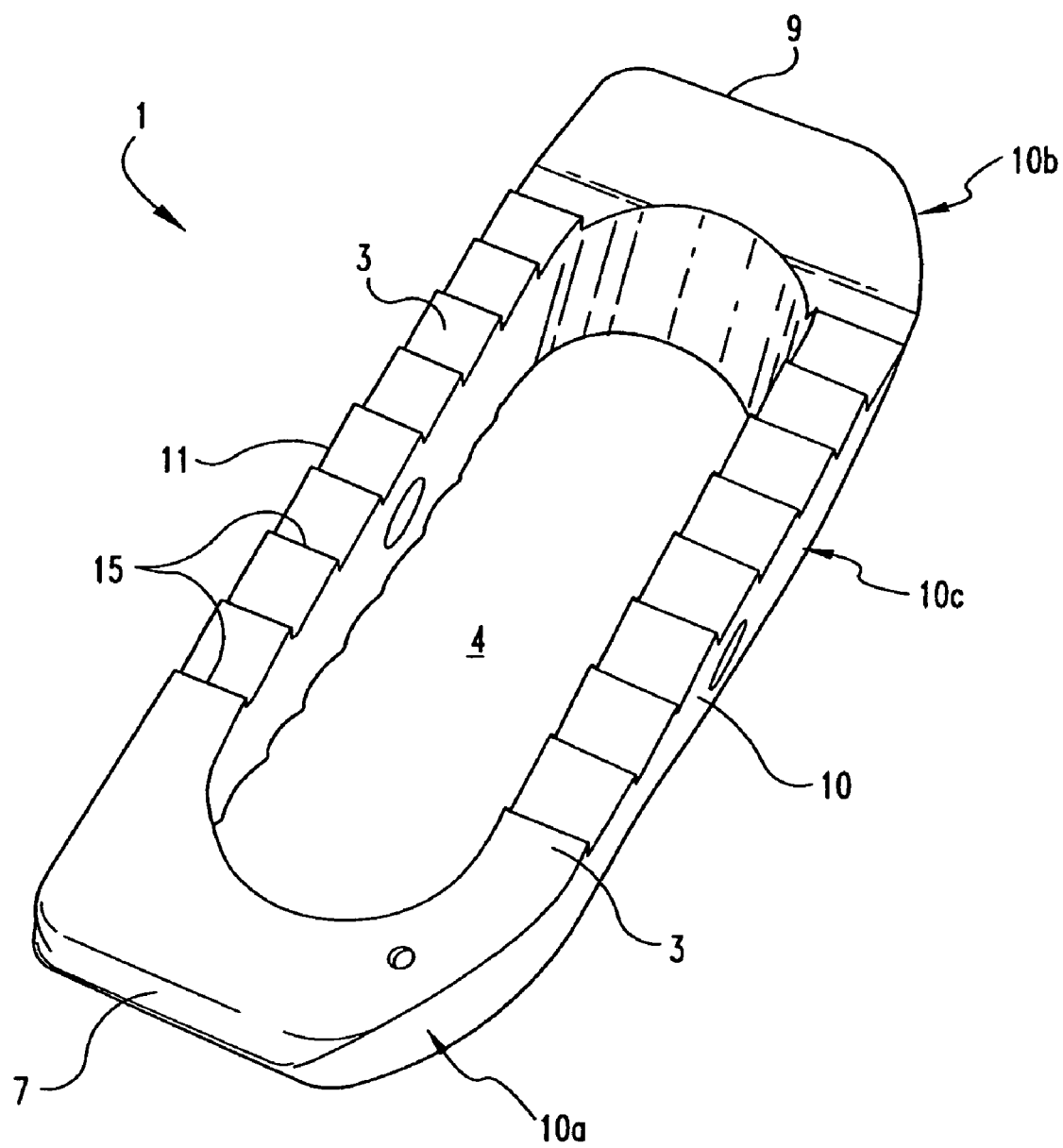
FIG. 1 is a perspective view of an implant of an embodiment of the invention.

FIGS. 1-4 illustrate an implant 1 with an elongated body positionable in a spinal disc space. A convexly curved upper surface 3 orientable toward an endplate of an upper vertebra and a convexly curved lower surface 5 orientable toward an endplate of a lower vertebra are shown. In some embodiments, the upper and lower curvatures are mirror images of one another, or the curvatures may be different. For example, the upper curvature may be greater than the lower curvature to better match a more pronounced curvature in the inferior endplate of a superior vertebra and a less pronounce curvature in the superior endplate of an inferior vertebra. The upper surface 3 and lower surface 5 may have constant radii, may be compound curves, or may one or both be flat.

As shown in FIGS. 1-4, the upper and lower surfaces 3, 5 are broken by a cavity 4. The cavity 4 may partially or fully penetrate the implant 1. In the illustrated embodiment, the upper surface 3 and the lower surface 5 have portions on all sides of the cavity 4. Although in some illustrations, for clarity, the surfaces may only be labeled on a single side, the surfaces are intended to include portions beyond each extent of the cavity 4. As shown, the upper surface 3 and the lower surface 5 are convexly curved along an entire length of the body of the implant 1. The term "entire length" does not include various extensions or truncations near the ends of the implant 1 in some embodiments. In other embodiments of the invention, curves may be convex for only portions of the length, or other shapes may be interspersed between convex portions, or an overall convex shape may be formed by flat or variously shaped segments to generate and overall convex shape.

A leading end portion 7 and an opposite trailing end portion 9 are also shown in FIGS. 1-4. The leading end portion 7 illustrated has a rounded nose between the upper surface 3 and the lower surface 5. The nose on the leading end shown is also partially rounded between an anterior sidewall 10 and a posterior sidewall 11. In some embodiments, the nose may be completely rounded between the sidewalls, or in others may include flat portions. The illustrated trailing end portion 9 is planar and extends between the anterior and posterior sidewalls 10, 11. In other embodiments, the trailing end portion may be curved, angular, or any other functional shape.

The anterior sidewall 10 extends between the leading end portion 7 and the trailing end portion 9, and the anterior sidewall 10 shown is at least partially convexly curved. As illustrated in FIG. 1, the anterior sidewall 10 is defined by a maximally anterior portion 10c, a first curved portion 10a extending between the leading end portion 7 and the maximally anterior portion 10c, and a second curved portion 10b extending between the trailing end portion 9 and the maximally anterior portion 10c. As shown, the first and second curved portions 10a, 10b are convex curves, and the maximally anterior portion 10c is a flat segment. In other embodiments, the first and second curved portions 10a, 10b may be a part of the same convex curve and the maximally anterior portion 10c may be a point along the curve. Alternatively, there may be only one of the first and second curved portions 10a, 10b composing the anterior sidewall 10, or the sidewall may be a combination of segments of various shapes. In some embodiments, the convex curve of the anterior sidewall 10 will include more than rounded corners or chamfers.

Figure 33:
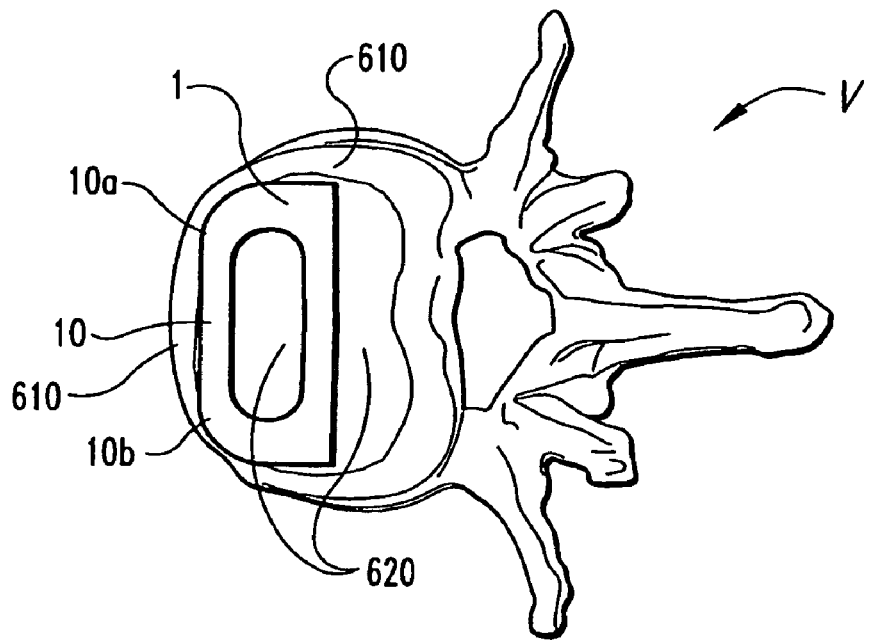
FIG. 33 is a plan view of a vertebral endplate and an outline of an implant of an embodiment of the invention.
Figure 34:
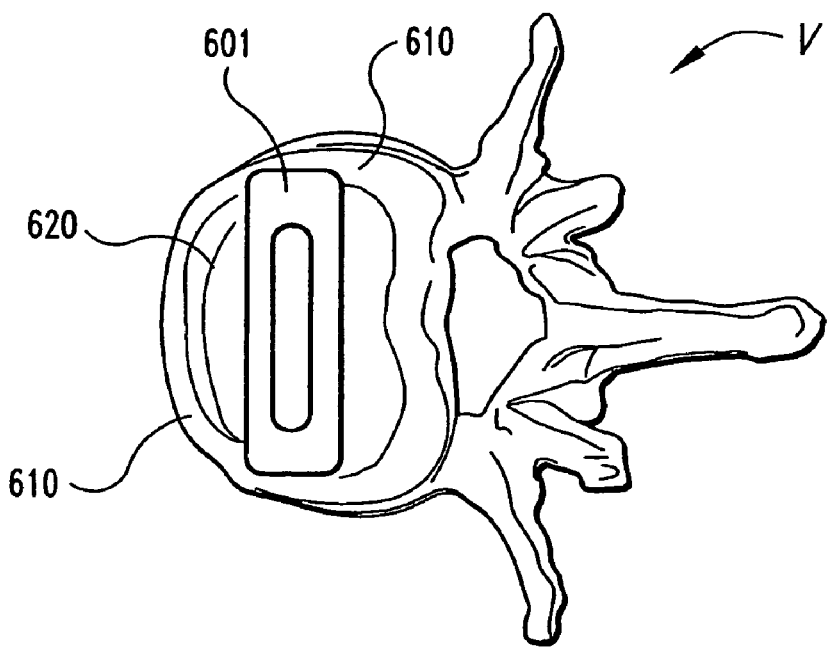
FIG. 34 is a plan view of a vertebral endplate and an outline of an implant of an embodiment of the invention.

In some embodiments, the curvature of the anterior sidewall 10 is useful to permit the implant 1, and particularly first and second curved portions 10a, 10b, to be substantially located between the cortical rims of the supported vertebrae without extending beyond the bounds of the cortical rims. Referring to FIG. 33, a cortical rim 610 extends around the periphery of an anterior portion of an inferior vertebral body V. Because first and second curved portion 10a, 10b are curved, the implant 1 is capable of being positioned more anteriorly and more along the cortical rim 610. The cortical rim 610 provides more support than the interior, cancellous bone 620 of the vertebral body V. An alternate placement for an implant is illustrated in FIG. 34. An alternate implant 601 is shown placed from a lateral approach, but placed more posteriorly on the vertebral body V.

The posterior sidewall 11 shown extends between the leading end portion 7 and the trailing end portion 9 of the implant 1. The body of the implant 1 includes a height between the upper and lower surfaces 3, 5 corresponding to a desired disc space height between the upper vertebra endplate and the lower vertebra endplate. The term "height" refers to a distance between the upper and lower surfaces 3, 5. In some embodiments, the upper and lower surfaces 3, 5 are not planar and are not a constant distance from one another. Therefore, the term height is not limited to a specific distance, but may be used to describe an overall shape that produces a desired separation of the vertebrae.

In some embodiments, at least one of the upper surface 3 and the lower surface 5 are curved such that the height of the implant 1 near its center is greater than the height of the implant 1 near its leading end portion 7. For an implant such as implant 1 that includes a lordotic configuration, the height of the implant near its center is the maximum height of the implant near its center. As shown in FIGS. 1-4, the height is the height of the anterior sidewall 10 near its center. For an implant such as non-lordotic implant 101 (FIG. 5), the height of the implant near its center is the height of either the anterior sidewall 110 or the posterior sidewall 111 near either of their centers. For example, the height of the non-lordotic implant 101 (FIG. 5) near its center is labeled as $h_i$. The height of the implant 1 near its leading end portion 7 is the maximum distance between the upper surface 3 and the lower surface 5 prior to any rounded or pointed portions of the leading end portion 7 such as a nose. For example, the height of the non-lordotic implant 101 (FIG. 5) near its leading end portion is labeled as $h_n$.

The height of an implant of embodiments of the invention near the center of the implant is between about 7 mm and 19 mm, and the height of such an implant near the leading end is at least about 3 mm less than the height of the respective implant near its center. For example, an implant with a height of 12 mm near its center would have a height of 9 mm or less near its leading end. In another specific embodiment, the height of an implant near its center is between about 13 mm and 19 mm, and the height of the implant at its leading end is between about 4 mm and 9 mm. For another embodiment, the height of an implant near its center is between about 9 mm and 13 mm, and the height of the implant at its leading end is between about 4 mm and 7 mm. In yet another embodiment, the height of an implant near its center is between about 6 mm and 9 mm, and the height of the implant at its leading end is between about 3 mm and 5 mm. In still another embodiment, the height of an implant of embodiments of the invention near the center of the implant is between about 8 mm and 14 mm, and the height of such an implant near the leading end is at least about 3 mm less than the height of the respective implant near its center.

The leading end portion 7 of some embodiments of the invention is structured for insertion into the disc space in an at least partially collapsed condition. The height of the implant 1, including the leading end portion 7 in such embodiments is sized to restore the collapsed disc space to the desired disc space height as the body is inserted in the collapsed disc space. The leading end portion 7 may facilitate insertion due to a relatively short height, and an increasing height along the length of the implant 1 will restore the collapsed disc space.

As illustrated in FIGS. 1-4, an average height of the anterior sidewall 10 is greater than an average height of the posterior sidewall 11. When implanted by some methods, this facilitates the implant 1 providing lordotic correction between vertebrae. FIGS. 33 and 34 show placements of devices that would create lordotic correction for an implant with an anterior sidewall of greater average height than its posterior sidewall. In other embodiments, the anterior and posterior sidewalls may be the same height, or the posterior sidewall may be of greater height in part or on average. A posterior wall of greater height could be useful in portions of the spine where a kyphotic curvature is desirable, to correct a deformity, or to provide treatment for a traumatic injury.

The implant 1 may include a number of engagement members 15 along it upper surface 3 and/or lower surface 5. The engagement members 15 shown in FIGS. 1-4 project outwardly from the upper and lower surfaces 3, 5 to engage bony tissue of the adjacent vertebral endplate when the implant 1 is positioned in the spinal disc space. The engagement members 15 illustrated are a number of teeth along the cavity 4 that are raked toward the direction of implant insertion. Engagement members 15 may be teeth or other projections or voids that create some resistance to movement, including such elements as a friction coating or friction surface treatment. The engagement members 15 illustrated are raked toward the direction of implant insertion to resist expulsion of the implant through the insertion incision with less resistance to insertion, but the engagement members may be configured to resist movement in any direction.

Figure 2:
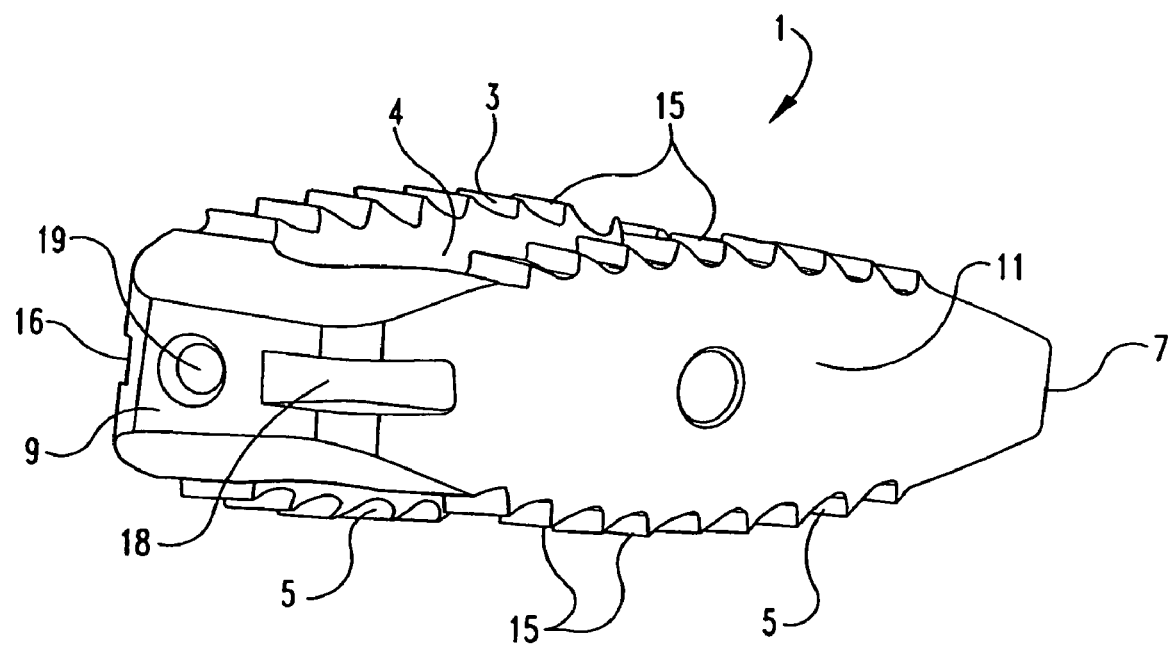
FIG. 2 is another perspective view of the implant of FIG. 1.
Figure 3:
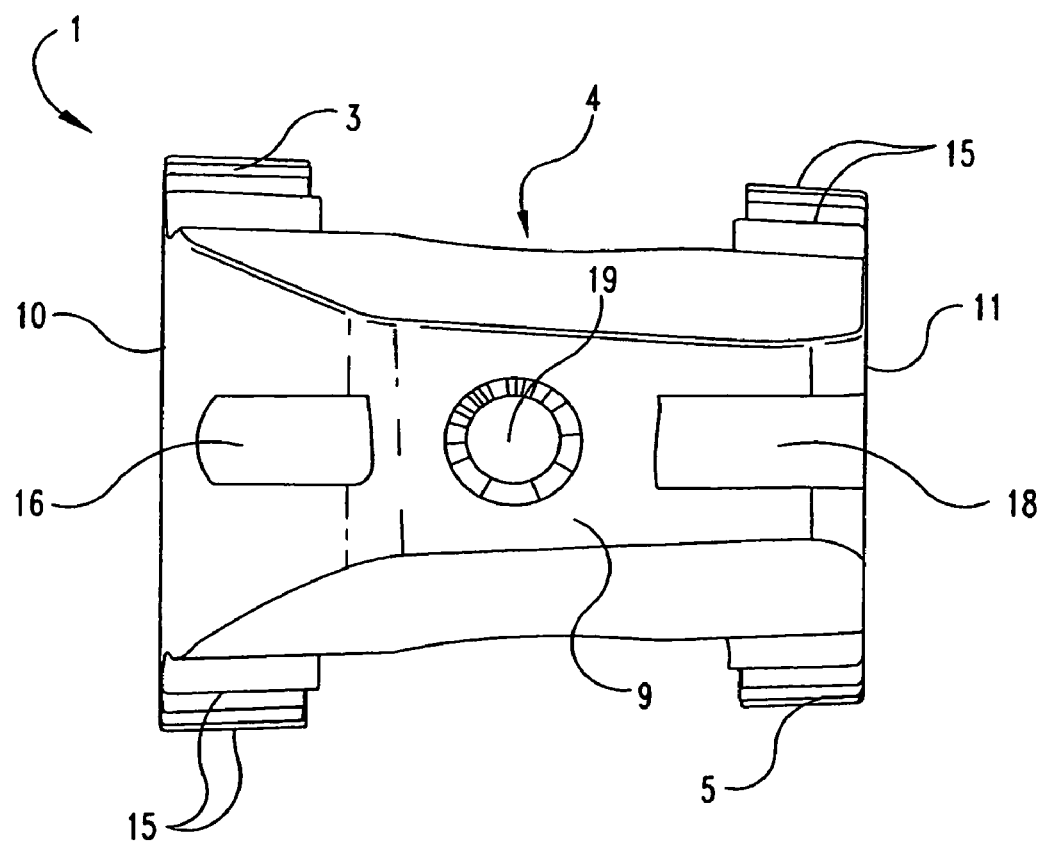
FIG. 3 is an end elevation view of the implant of FIG. 1.
Figure 4:
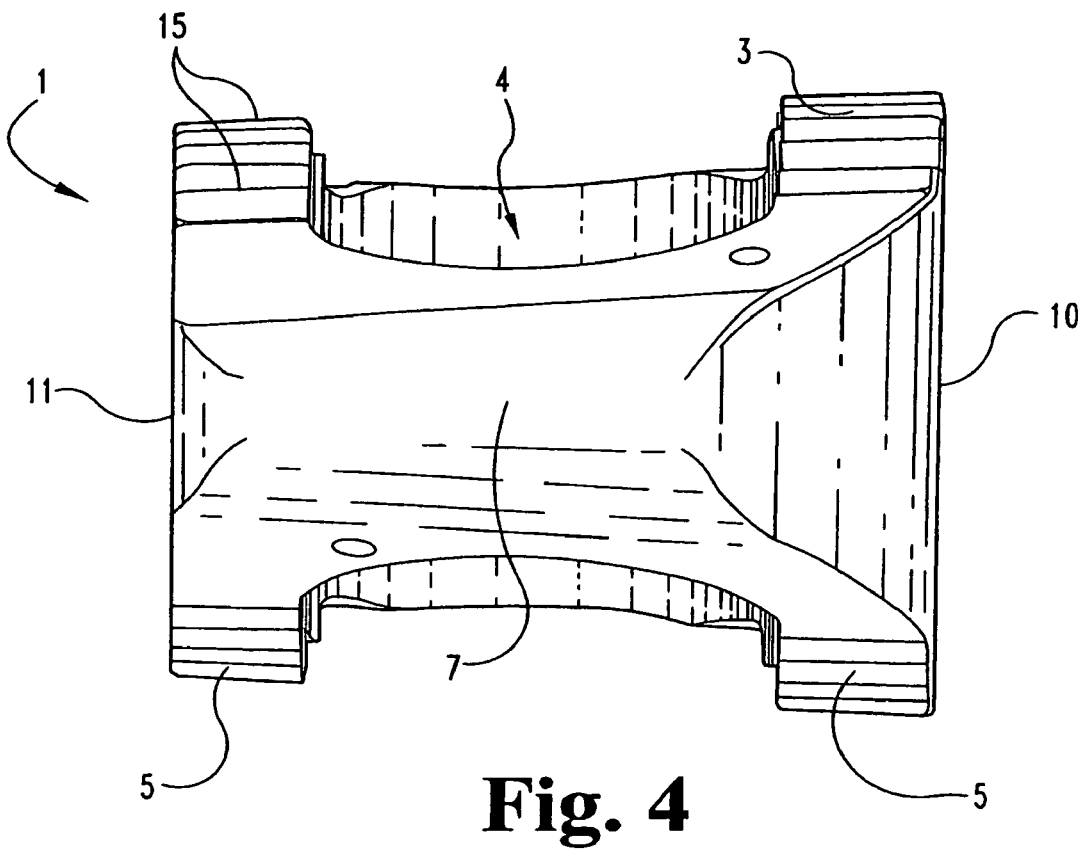
FIG. 4 is an end elevation view of the implant of FIG. 1.

As shown in FIGS. 2 and 3, the implant 1 includes a first notch 16 in the anterior sidewall 10, and a second notch 18 in the posterior sidewall 11. The illustrated first and second notches 16, 18 have flat upper and lower surfaces, but the notches may be of any configuration that facilitates gripping of the implant 1 with a coupling member. The coupling member may include some or all of the elements of the insertion instrument 550 (FIG. 8) or other such devices. The coupling member may have first and second fingers 568, 570 positionable in respective ones of the first and second notches 16, 18 to secure the body of the implant 1 to the coupling member. In some embodiments, the coupling member is incorporated with the implant 1 for insertion into the disc space. A securing mechanism 19 is incorporated in some embodiments of the invention. The securing mechanism 19 may be a threaded hole for receiving a threaded shaft or screw. The securing mechanism may also be configured to provide an interference fit or any other device for engagement with a coupling member to facilitate connection with the coupling member.

Figure 5:
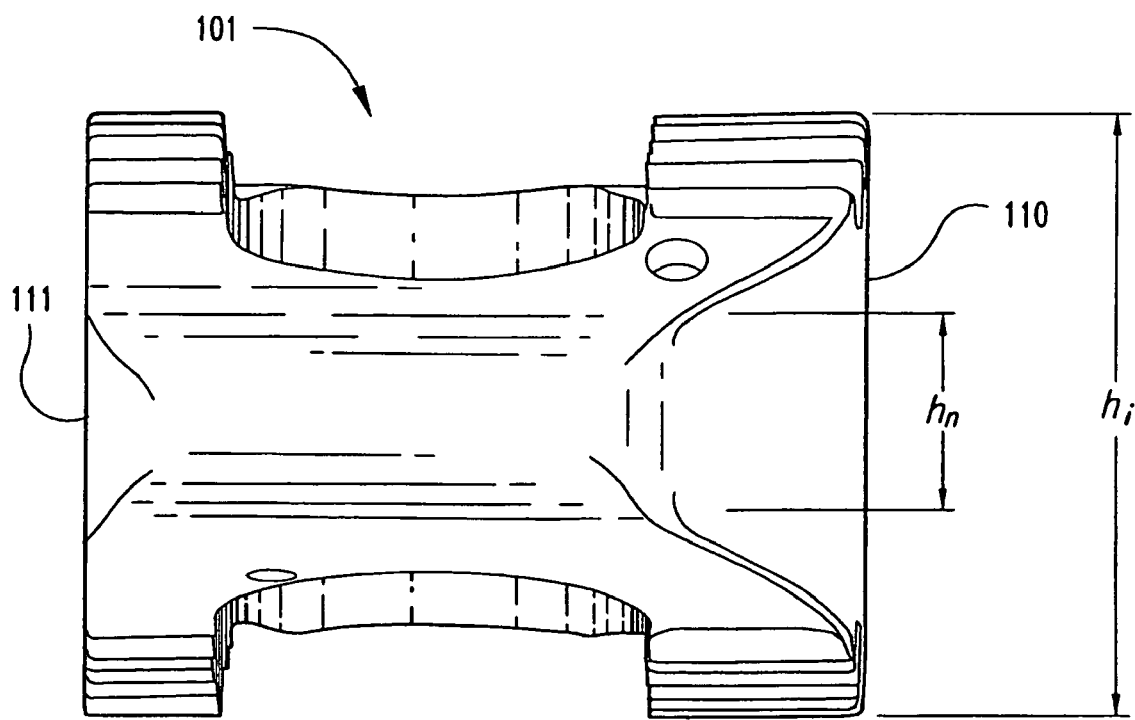
FIG. 5 is an end elevation view of an implant of another embodiment of the invention.

Referring to FIG. 5, another embodiment of an implant of the invention is illustrated. The non-lordotic implant 101 has an anterior sidewall 110 and a posterior sidewall 111 that are substantially the same height. Such an implant may be useful to provide vertebral spacing in clinical circumstances where lordotic correction is not necessary. Other features and configurations of the non-lordotic implant 101 are similar to the features and configurations of the implant 1 described above.

Figure 6:
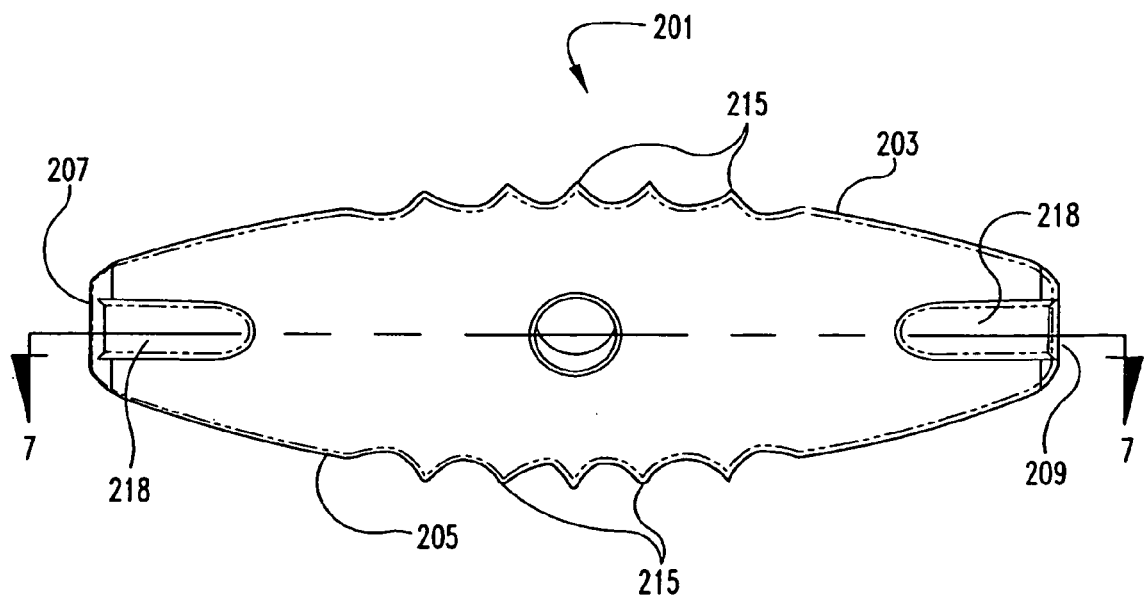
FIG. 6 is an elevation view of still another implant of an embodiment of the invention.
Figure 7:
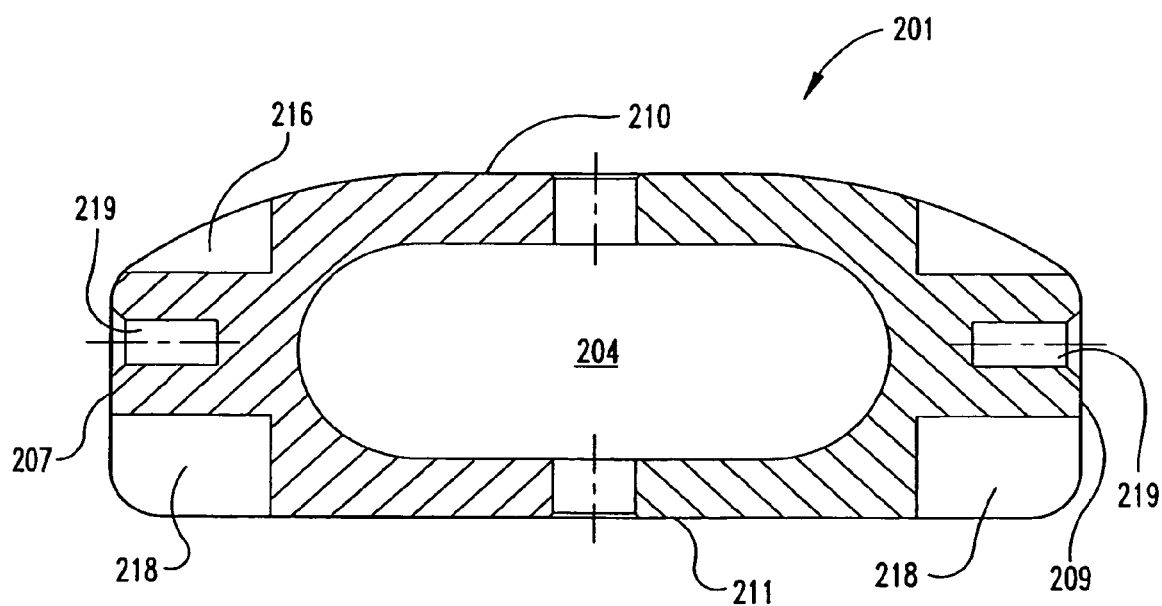
FIG. 7 is a cross-sectional view of the implant of FIG. 6.

Another embodiment of the invention is illustrated in FIGS. 6 and 7. A symmetrical implant 201 has an elongated body positionable in a spinal disc space. A convexly curved upper surface 203 orientable toward an endplate of an upper vertebra and a convexly curved lower surface 205 orientable toward an endplate of a lower vertebra are shown. In some embodiments, the upper and lower curvatures are mirror images of one another, or the curvatures may be different. For example, the upper curvature may be greater than the lower curvature to better match a more pronounced curvature in the inferior endplate of a superior vertebra and a less pronounce curvature in the superior endplate of an inferior vertebra. The upper surface 203 and lower surface 205 may have constant radii, may be compound curves, or may one or both be flat.

As shown in FIG. 7, the upper and lower surfaces 203, 205 are broken by a cavity 204. The cavity 204 may partially or fully penetrate the symmetrical implant 201. In the illustrated embodiment, the upper surface 203 and the lower surface 205 have portions on all sides of the cavity 204. Although in some illustrations, for clarity, the surfaces may only be labeled on a single side, the surfaces are intended to include portions beyond each extent of the cavity 204. As shown, the upper surface 203 and the lower surface 205 are convexly curved along an entire length of the body of the symmetrical implant 201. The term "entire length" does not include various extensions or truncations near the ends of the symmetrical implant 201 in some embodiments. In other embodiments of the invention, curves may be convex for only portions of the length, or other shapes may be interspersed between convex portions, or an overall convex shape may be formed by flat or variously shaped segments to generate and overall convex shape.

A first end portion 207 and an opposite second end portion 209 are also shown in FIGS. 6 and 7. The symmetrical implant 201 is capable of insertion with either the first or second end portions 207, 209 being inserted into the disc space first. Likewise, either the first or second end portions 207, 209 may be coupled to an insertion instrument. Surgeons may at different times want to approach patients from the left or right side. An implant configured symmetrically may be useful, for among other purposes, to reduce inventory where implants are required with differently shaped upper and lower surfaces 203, 205.

The anterior sidewall 210 and posterior sidewall 211 configurations are similar to the anterior sidewall 10 and posterior sidewall 11 described in detail above and all features may be applied to any embodiment.

The first and second end portions 207, 209 of some embodiments of the invention are structured for insertion into the disc space in an at least partially collapsed condition. The height of the symmetrical implant 201, including the end portion inserted, is sized to restore the collapsed disc space to the desired disc space height as the body is inserted in the collapsed disc space. The end portion inserted may facilitate insertion due to a relatively short height, and an increasing height along the length of the implant 201 will restore the collapsed disc space.

The symmetrical implant 201 may include a number of engagement members 215 along it upper surface 203 and/or lower surface 205. The engagement members 215 shown in FIG. 6 project outwardly from the upper and lower surfaces 203, 205 to engage bony tissue of the adjacent vertebral endplate when the symmetrical implant 201 is positioned in the spinal disc space. The engagement members 215 illustrated are a number of teeth along the cavity 204. Engagement members 215 may be teeth, including raked teeth, or other projections or voids that create some resistance to movement, including such elements as a friction coating or friction surface treatment. The engagement members may be configured to resist movement in any direction.

As shown in FIG. 7, the symmetrical implant 201 includes a first notch 216 in the anterior sidewall 210, and a second notch 218 in the posterior sidewall 211 at both the first end portion 207 and the second end portion 209. The illustrated first and second notches 216, 218 have flat upper and lower surfaces, but the notches may be of any configuration that facilitates gripping of the implant 1 with a coupling member. The coupling member may include some or all of the elements of the insertion instrument 550 (FIG. 8) or other such devices. The coupling member may have first and second fingers 568, 570 positionable in respective ones of the first and second notches 216, 218 to secure the body of the symmetrical implant 201 to the coupling member. In some embodiments, the coupling member is incorporated with the symmetrical implant 201 for insertion into the disc space. A securing mechanism 219 is incorporated in some embodiments of the invention. The securing mechanism 219 may be a threaded hole for receiving a threaded shaft or screw. The securing mechanism may also be configured to provide an interference fit or any other device for engagement with a coupling member to facilitate connection with the coupling member.

Figure 8:
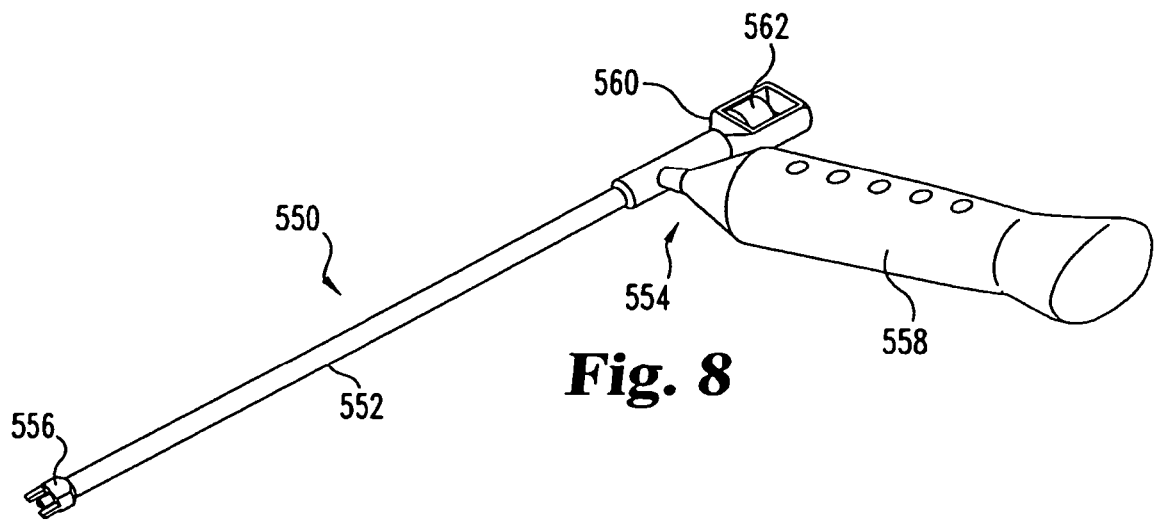
FIG. 8 is a perspective view of a coupling member of an embodiment of the invention.
Figure 9:
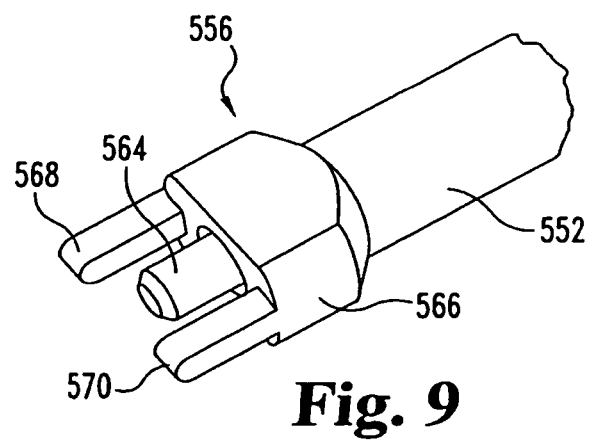
FIG. 9 is a perspective view of a distal end of the coupling member of FIG. 8.

Referring to FIG. 8, there is shown an insertion instrument 550. Insertion instrument 550 includes an elongated shaft 552 extending between a proximal portion 554 and a distal gripping portion 556 that serves as a coupling member to couple an implant such as the implant 1 to shaft 552. Proximal portion 554 includes a handle 558 extending transversely to shaft 552. In one embodiment, handle 558 is obliquely oriented to shaft 552 to facilitate manipulation and gesturing with insertion instrument 550. Shaft 552 projects proximally from handle 558 to a housing portion 560. Housing portion 560 includes an adjustment member 562 housed therein. An inner shaft 564 (FIG. 9) extends distally from adjustment member 562 and through shaft 552 to distal gripping portion 556. Adjustment member 562 provides a thumbwheel or other suitable gripping element to facilitate the surgeon rotating inner shaft 564 within outer shaft 552 for engagement of the distal end of inner shaft 564 with an implant.

Figure 10:
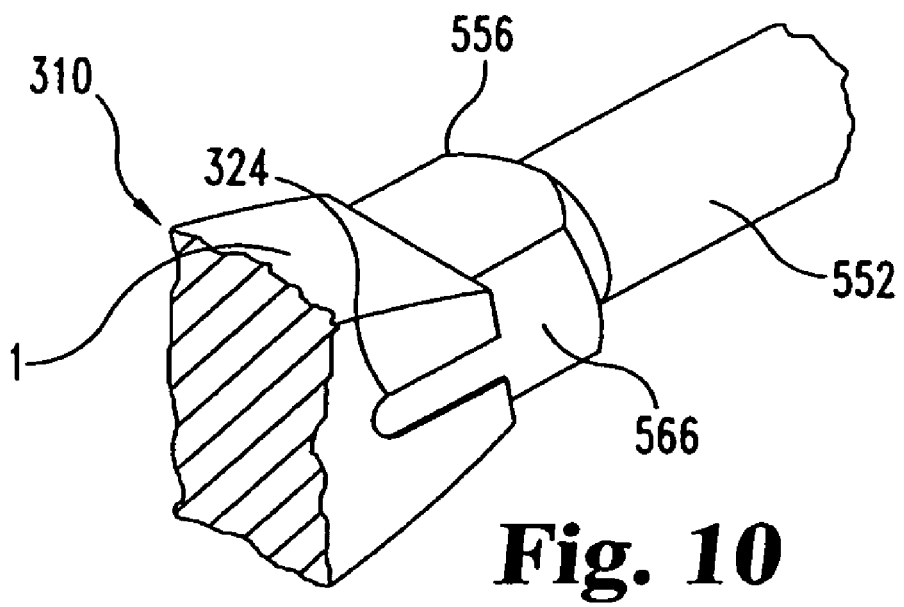
FIG. 10 is a perspective view of a coupling member of an embodiment of the invention attached to an implant.

Distal gripping portion 556 includes a body member 566 and a pair of fingers 568, 570 extending distally from opposite sides of body member 566. The distal end of inner shaft 564 projects distally from the body member 566 and is centrally located between fingers 568, 570. As shown in FIG. 10, fingers 568, 570 are positionable in respective ones of the notches of the implant to which insertion instrument 550 is engaged, such as implant 1 in the illustrated embodiment. Inner shaft 564 is engageable in a bore in the proximal end wall of an implant, such as securing mechanism 19 of implant 1. The outer surfaces of fingers 568, 570 are flush or recessed relative to the outer lateral surfaces of sidewalls of the implant 1 such that fingers 568, 570 do not protrude beyond the sidewalls of the implant 1. When engaged to the implant 1, fingers 568, 570 define an overall width that is less than the width of the implant between the outer lateral surfaces of its sidewalls. This minimizes the insertion profile of the implant and instrument assembly, and facilitates a less invasive approach to the spinal disc space.

Figure 11:
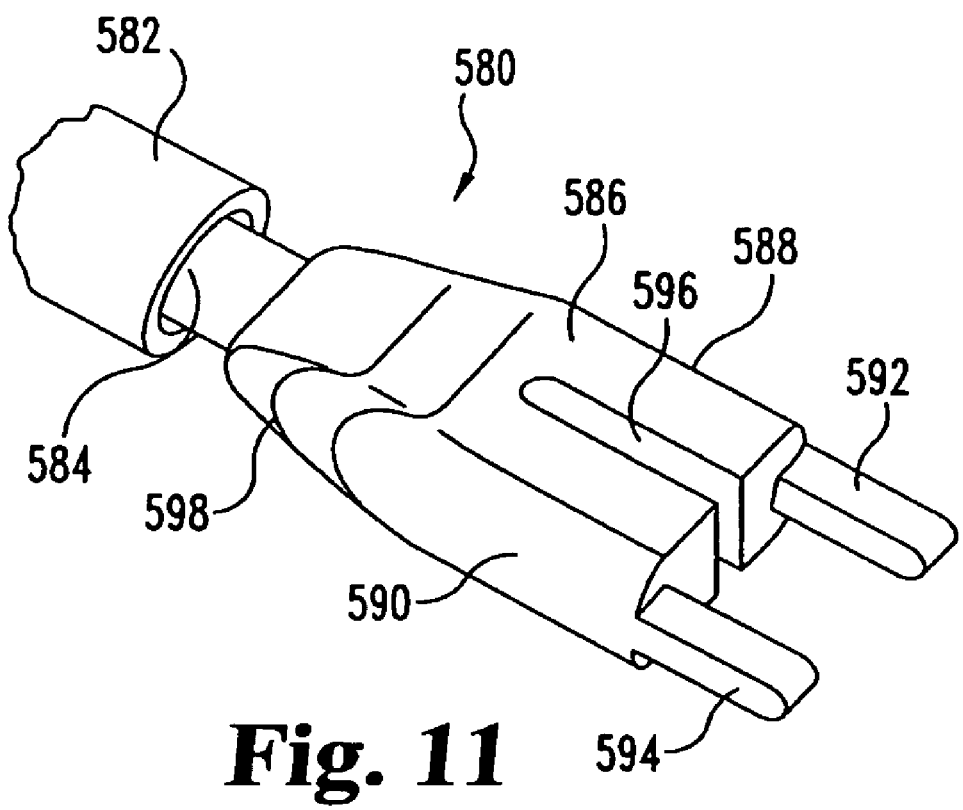
FIG. 11 is a perspective view of the distal end of a coupling member of another embodiment of the invention.

Referring to FIG. 11, there is shown another embodiment insertion instrument 580. Insertion instrument 580 includes an outer shaft 582 longitudinally movable about an inner shaft 584. Insertion instrument 580 includes a distal gripping portion 586 that forms a coupling member for coupling an implant to inner shaft 584. Distal gripping portion 586 includes a body member at a distal end of inner shaft 584 that includes a base portion 598 and a pair of biasing members 588, 590 separated by a central slot 596. Biasing members 588, 590 are coupled to one another about a living or integral hinge formed at base portion 598. Fingers 592, 594 extend distally from respective ones of the biasing members 588, 590. Base portion 598 includes a proximally tapered outer surface profile. Outer shaft 582 is movable distally relative to inner shaft 584 and along the outer surface profile of at least base portion 598 to move biasing members 588, 590 and thus fingers 592, 594 toward one another to grip an implant therebetween. The implant can be released by proximally displacing outer shaft 582 relative to inner shaft 584 to allow biasing members 588, 590 and thus fingers 592, 594 to move away from one another toward their normal state.

Various mechanisms for moving outer shaft 582, 584 are contemplated. For example, shafts 582, 584 can be threadingly engaged to one another and outer shaft 584 is rotated about inner shaft 582 to effect proximal and distal movement therebetween. In another example, proximal handle actuators are coupled to inner and outer shaft 582, 584, and the handles effect proximal and distal linear movement between the shafts as the handles are manipulated. Other suitable mechanisms for moving the inner and outer shafts longitudinally relative to one another are also contemplated.

Figure 12:
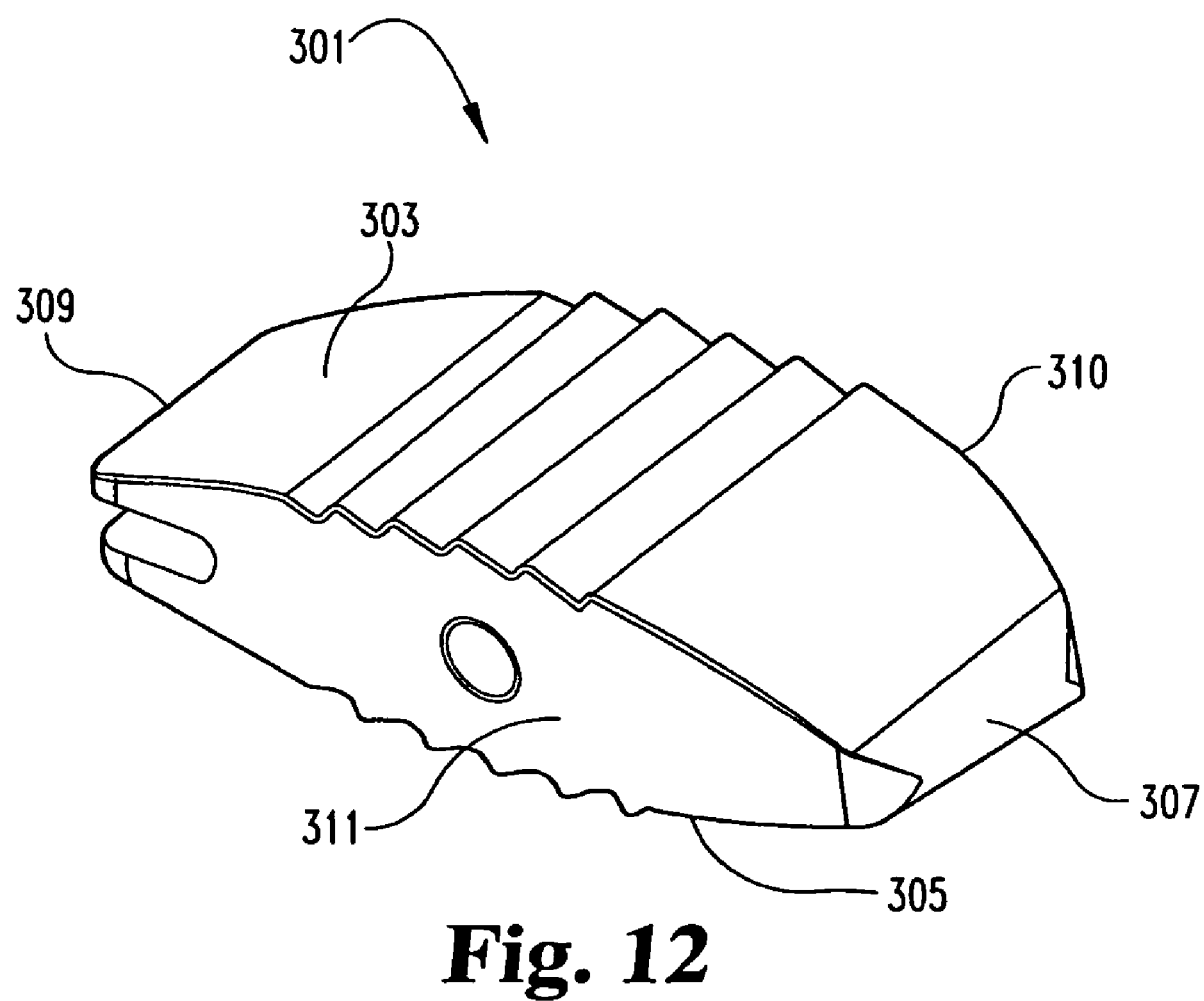
FIG. 12 is a perspective view of an implant of another embodiment of the invention.

Referring to FIG. 12, a graft implant 301 is illustrated with an elongated body positionable in a spinal disc space. The embodiment has a convexly curved upper surface 303 orientable toward an endplate of an upper vertebra, a convexly curved lower surface 305 orientable toward an endplate of a lower vertebra, a leading end portion 307, and an opposite trailing end portion 309. An at least partially convexly curved anterior sidewall 310 extends between the leading end portion 307 and the trailing end portion 309, and a posterior sidewall 311 extends between the leading end portion 307 and the trailing end portion 309. The graft implant 301 includes a height between the upper and lower surfaces 303, 305 corresponding to a desired disc space height between the upper vertebra endplate and the lower vertebra endplate. The leading end portion 307 is structured for insertion into the disc space in an at least partially collapsed condition and the height is sized to restore the collapsed disc space to the desired disc space height as the graft implant 301 is inserted in the collapsed disc space.

The graft implant 301 shares configurations, functions, and descriptions with the implant 1 described in detail above. Additionally, embodiments of the graft implant 301, and other embodiments described herein, may be constructed of bone graft materials. Without limitation, the bone graft material may be allograft bone. In some embodiments, the graft implant 301 is constructed of a solid section of bone. In other embodiments, the graft implant 301 is constructed of planks of bone that are assembled into a final configuration. The graft implant 301 may be constructed of planks of bone that are assembled along horizontal or vertical planes through one or more longitudinal axes of the graft implant 301. In some embodiments, a cavity is cut or constructed through the graft implant 301. The cavity may be useful to contain grafting materials.

Embodiments of the implant include a device with an upper surface means, a lower surface means, a leading end means, an opposite trailing end portion, and an at least partially convexly curved anterior sidewall means. The trial bodies of the trial instruments and the implant bodies can be made from any biocompatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well. If the trial instrument or implant is made from radiolucent material, radiographic markers can be located on the trial instrument or implant to provide the ability to monitor and determine radiographically or fluoroscopically the location of the body in the spinal disc space. The material comprising the trial bodies can be solid, porous, spongy, perforated, drilled, and/or open.

There is contemplated an implant for insertion into a spinal disc space between adjacent vertebrae. The implant can be impacted or pushed into the disc space. The implant can be provided with a distal end or leading insertion end that is sized for insertion into the collapsed disc space. As the implant is inserted, the implant can restore the collapsed disc space to a desired disc space height. The desired disc space height corresponds to the height of the implant proximal the distal end. Once inserted, the implant can maintain the disc space at the desired disc space height.

There is further contemplated an implant that, when inserted, restores and maintains a desired disc space height of a collapsed disc space between an upper vertebra and a lower vertebra. The implant includes a body with a distal end, a proximal end, an upper surface orientable toward an endplate of the upper vertebra and a lower surface orientable toward an endplate of the lower vertebra. The body of the implant has a first height between the upper and lower surfaces corresponding to the desired disc space height. The body of the implant also has a second height at its distal end that is less than a height of the collapsed disc space.

It is contemplated that the implants can be provided with bi-convex curvature of the upper and lower surfaces, allowing the implants to center in the endplates of the disc space. It is further contemplated that the upper and lower surfaces of the implant can be planar or include compound geometry. The upper and lower surfaces of the implant can also be configured to establish lordotic or kyphotic angulation between the adjacent vertebral bodies.

It is contemplated that an insertion instrument can be engaged to lateral walls of an intervertebral implant. The insertion instrument includes a distal coupling portion positionable in notches formed in corresponding ones of the lateral walls of the implant. The coupling portion has a first position engaging the implant in the notches and a second position disengaged from the implant in the notches. The width of the coupling portion in each of its first and second positions is less than the width of the implant between the lateral walls of the implant.

An embodiment of the invention is a system for placing an implant between an endplate of an upper vertebra and an endplate of a lower vertebra that includes a trial instrument set and an implant. The implant of the system may include any implant described above, such as implant 1, non-lordotic implant 101, symmetrical implant 201, or graft implant 301, or any other implant compatible with the system set forth herein.

Figure 13:
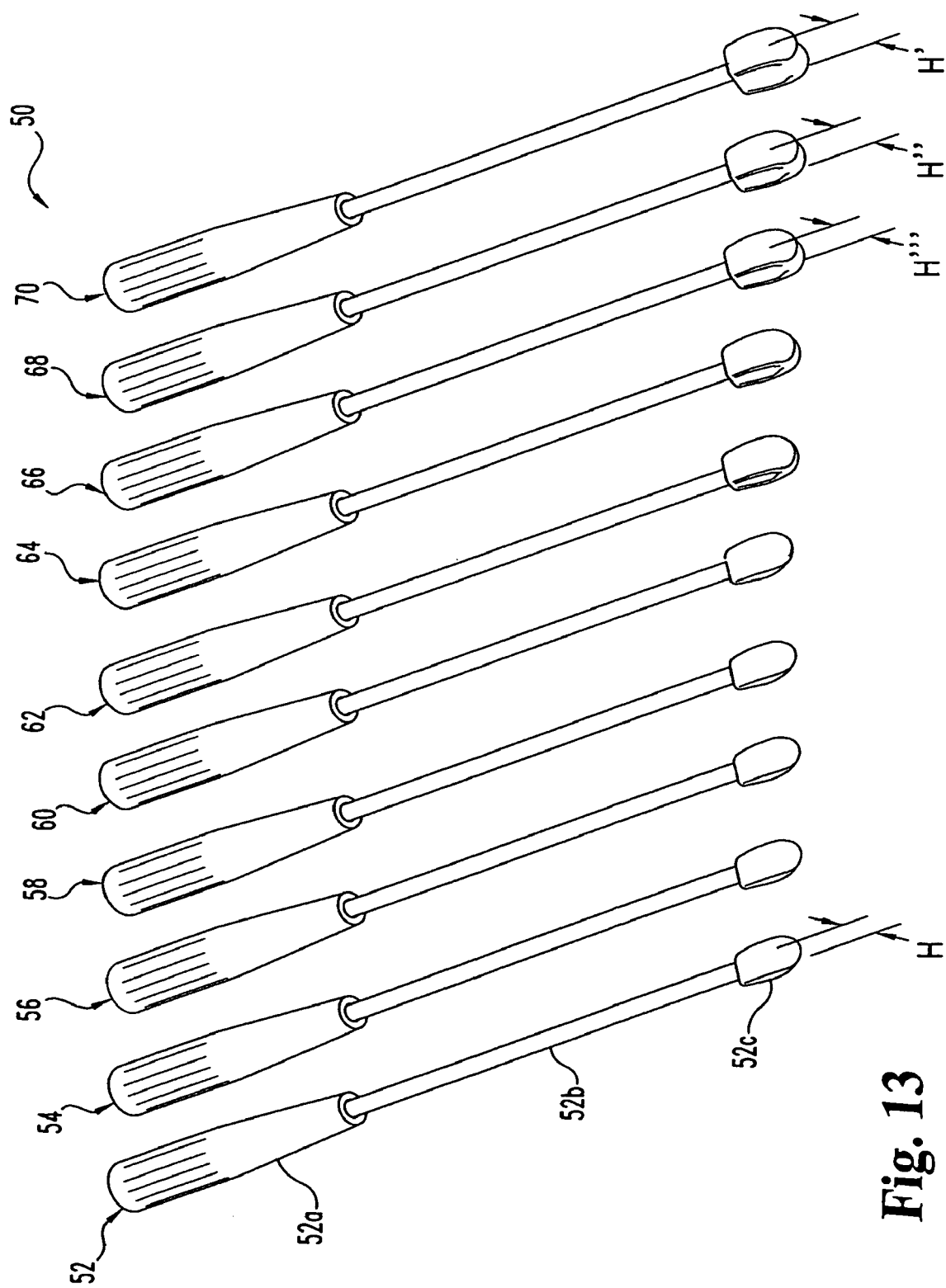
FIG. 13 is a perspective view of a set of instruments of an embodiment of the invention.
Figure 13A:
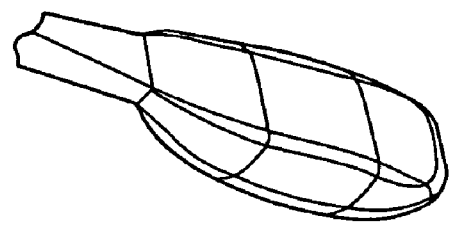
FIG. 13*a* is a perspective view of a distal portion of a trial instrument of an embodiment of the invention.
Figures 13B, 13C:
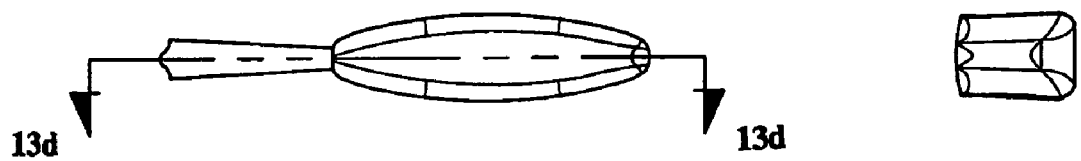
Figure 13D:
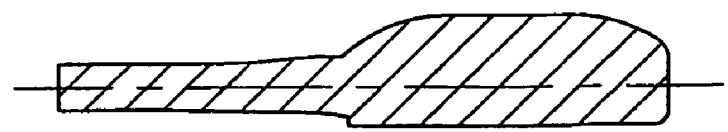
FIG. 13d is a cross-sectional view through line 13d-13d of FIG. 13b.

In FIG. 13 there is shown a trial instrument set 50 having a number of trial instruments 52, 54, 56, 58, 60, 62, 64, 66, 68 and 70. Trial instrument 52 includes a handle 52a, a shaft 52b extending distally from handle 52a, and a trial body 52c. Each of the other trial instruments also includes a handle, a shaft and a trial body. It is contemplated that each trial body of the trial instruments provides a different height between an upper and a lower contact surface thereof for restoring a collapsed disc space. As used herein, the term "trial instrument" with reference to the size or shape of the trial instrument may include the size or shape of the trial body. Trial instrument 52 can be provided with a trial body having the smallest height H of the instrument set 50, and trial instrument 70 can be provided with a trial body having the largest height H' of the instrument set 50. The remaining trial instruments can provide a number of different height trial instruments ranging in height between H and H'. In one particular embodiment of instrument set 50, the height of the trial instruments in the set increase in one millimeter increments. In another particular embodiment, the heights range from 6 millimeters to 19 millimeters in one millimeter increments. Other increments and other ranges of heights are also contemplated.

An embodiment of the trial instrument set 50 has at least two instruments of different sizes. As shown in FIGS. 13a-13d, instruments of the trial instrument set 50 may have an upper surface orientable toward the upper vertebra, a lower surface orientable toward the lower vertebra, and a leading end portion with segments that diverge from the leading end to meet the upper surface and the lower surface respectively.

As further shown in FIGS. 13a-13d, instruments of the trial instrument set 50 may have upper and/or lower surfaces with convex curvatures and may have a curve extending between their upper and lower surfaces. The curve extending between the upper and lower surface may be a radius or any other functional shape whether a curve is incorporated or not. In some embodiments, at least one of the trial instruments of the trial instrument set 50 is substantially the same shape as an implant of the system. At least one of the trial instruments of the trial instrument set 50 may be substantially the same shape as an implant of the system about either a horizontal or vertical plane of the implant, or about both planes.

The system may also include an access portal insertable through an incision. Such an access portal may provide a path through which a trial instrument, an implant, or both may be passed. The access portal may be a tubular port, a retractor, or any other mechanism for holding open an operative site. A tubular port 170 is shown in FIG. 14e. A retractor structure 180 is illustrated in FIG. 14f, and various embodiments are described in association with FIGS. 15-30.

Figure 16:
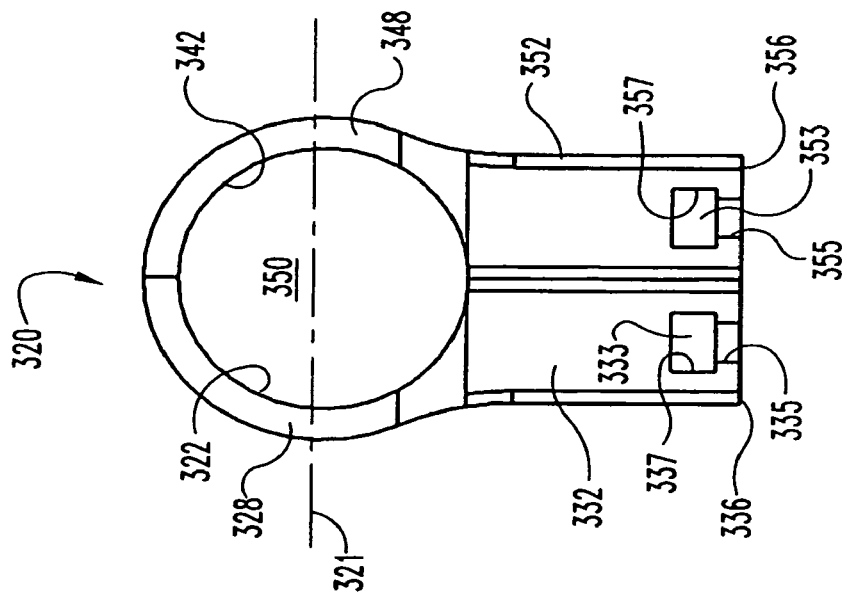
FIG. 16 is a plan view of the retractor of FIG. 15.
Figure 15:
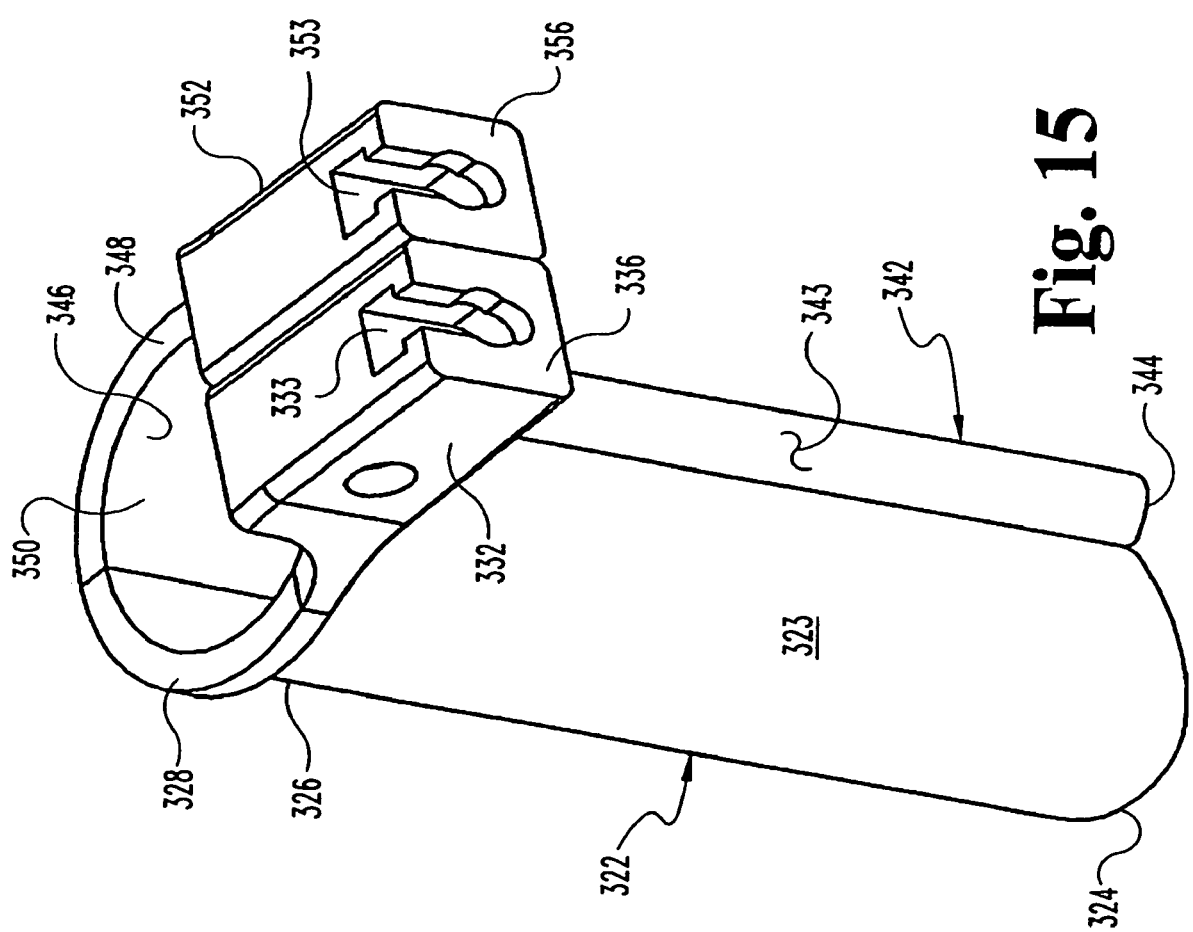
FIG. 15 is a perspective view of a retractor in an insertion configuration.

Referring to FIGS. 15 and 16, there is shown an embodiment of a retractor 320. Retractor 320 includes a first retractor portion 322 and a second retractor portion 342. First portion 322 includes a body 323 extending between a distal end 324 and an opposite proximal end 326. Second portion 342 includes a body 343 extending between a distal end 344 and an opposite proximal end 346. Distal ends 324, 344 can be beveled or distally tapered to facilitate insertion, although non-beveled ends are also contemplated. First portion 322 can be positioned adjacent to or mated with second portion 342 along adjacent ones of the longitudinal edges 325, 327 of first portion 322 and longitudinal edges 345, 347 of second portion 342. Other arrangements between the adjacent edges are also contemplated as discussed above. It is further contemplated that the longitudinal edges can be spaced from one another in the insertion configuration. A working channel 350 is formed between first portion 322 and second portion 342. Working channel 350 extends between and opens at distal ends 324, 344 and proximal ends 326, 346.

Retractor 320 is insertable through skin and tissue of a patient to provide working channel 350 to the surgical site. It is contemplated that retractor 320 is inserted through the skin and tissue in an insertion configuration for working channel 350, such as shown in FIGS. 15-18. In the insertion configuration, working channel 350 is substantially enclosed or circumscribed by first portion 322 and second portion 342. After insertion into the patient, working channel 350 can be enlarged by separating first portion 322 and second portion 342 away from one another along an axis 321 extending therebetween. Separation of first and second portions 322, 342 increases the size of working channel 350 from proximal ends 326, 346 to distal ends 324, 344. The first portion 322 and the second portion 342 may also include coupling structures (not shown) for coupling to at least one structure near a surgical site. A fastener, such as a bone screw, may be used to couple between either or both the first portion 322 and the second portion 342 and the structure near the surgical site. The coupling could be made before or after separation of the first and second portions 322, 342.

In the insertion configuration of FIGS. 15-18, working channel 350 is circumscribed or substantially enclosed by first portion 322 and second portion 342. Bodies 323 and 343 can be configured as discussed above with respect to the bodies of the portions of retractor 320. Working channel 350 can have a size in the insertion configuration that allows passage of one or more surgical instruments and/or implants to the surgical location in the patient's body, although smaller sizes are also contemplated. It may be desirable during surgery to provide greater access to the location in the patient's body beyond the locations provided through working channel 350 in its insertion configuration. Accordingly, first portion 322 and second portion 342 are movable away from one another along axis 321 to enlarge working channel 350.

First portion 322 includes body 323 with a semi-cylindrical shape extending between distal end 324 and proximal end 326. A collar 328 extends about proximal end 326, and forms a lip extending about the outer surface of body 323. Second portion 342 includes body 343 having a semi-cylindrical shape extending between distal end 344 and proximal end 346. A collar 348 extends about proximal end 346 of second portion 342, and defines a lip extending about the outer surface of body 343. It is further contemplated that first and second portions 322, 342 can be provided with or without a collar and/or a lip. First and second portions 322, 342 can also be provided with bracket members for engagement with an external arm that supports retractor 320 while positioned in the patient.

Extending from collar 328 of first portion 322 is a first engagement structure 332 having a head portion 336 forming a recess 333 therein. Extending from collar 348 of second portion 342 is a second engagement structure 352 having a head portion 356 forming a recess 353 therein. Engagement structures 332, 352 can be integrally formed with or removably engaged to the respective collars 328, 348. As discussed further below, an instrument for separating first portion 322 and second portion 342 can be non-releasably or releasably engaged to engagement structures 332, 352 for application of a separation force to enlarge working channel 350 by separating first portion 322 and second portion 342. Such an instrument could also be releasably or non-releasably engaged to first portion 322 and second portion 342. Engagement structures 332, 352 extend laterally from portions 322, 342 to facilitate allow engagement of a separation instrument to engagement structures 332, 352 without obstructing working channel 350 with the separation instrument. Such an instrument could also maintain first portion 322 and second portion 342 in the initial insertion configuration during and after insertion. The separation instrument can also maintain the enlarged configuration for working channel 350 in situ.

Recesses 333, 353 are adapted to receive engagement arms of the separation instrument engageable to portions 322, 342. In the illustrated embodiments, engagement structures 332, 352 extend laterally from and project proximally above the respective collar 328, 348. Engagement structures 332, 352 extend alongside one another and abut one another when portions 322, 342 are in their insertion configuration. Other configurations for the engagement structures are also contemplated, including engagement structures that are non-linear, that extend in directions away from one another when portions 322, 324 are in their insertion configuration, and engagement structures that do not abut one another in the insertion configuration.

Recesses 333, 353 open laterally to receive respective ones of the engagement arms of the separation instrument. Recess 333 includes a keyway opening 335 and a receptacle 337 in communication with opening 335. Receptacle 337 is enlarged relative to opening 335, and is shaped to receive a portion of the engagement arm of the separation instrument positioned therein. Similarly, recess 353 includes a keyway opening 355 and a receptacle 357 in communication with opening 355.

Receptacle 357 is enlarged relative to opening 355, and is shaped to receive a portion of the engagement arm of the separation instrument positioned therein. Openings 335, 355 and receptacles 337, 357 are open along the proximal sides of the respective engagement structures 332, 352 to facilitate placement of the separation instrument engagement arms therein. Other configurations for the recess 333, 353 are also contemplated, including recesses that are enclosed, uniform, or any other suitable configuration to receive a at least a portion of an engagement arm. Still other embodiments contemplate that engagement structures 332, 352 do not include recesses, but rather are shaped for receipt in or otherwise engage the respective engagement arm of the separation instrument.

Figure 19:
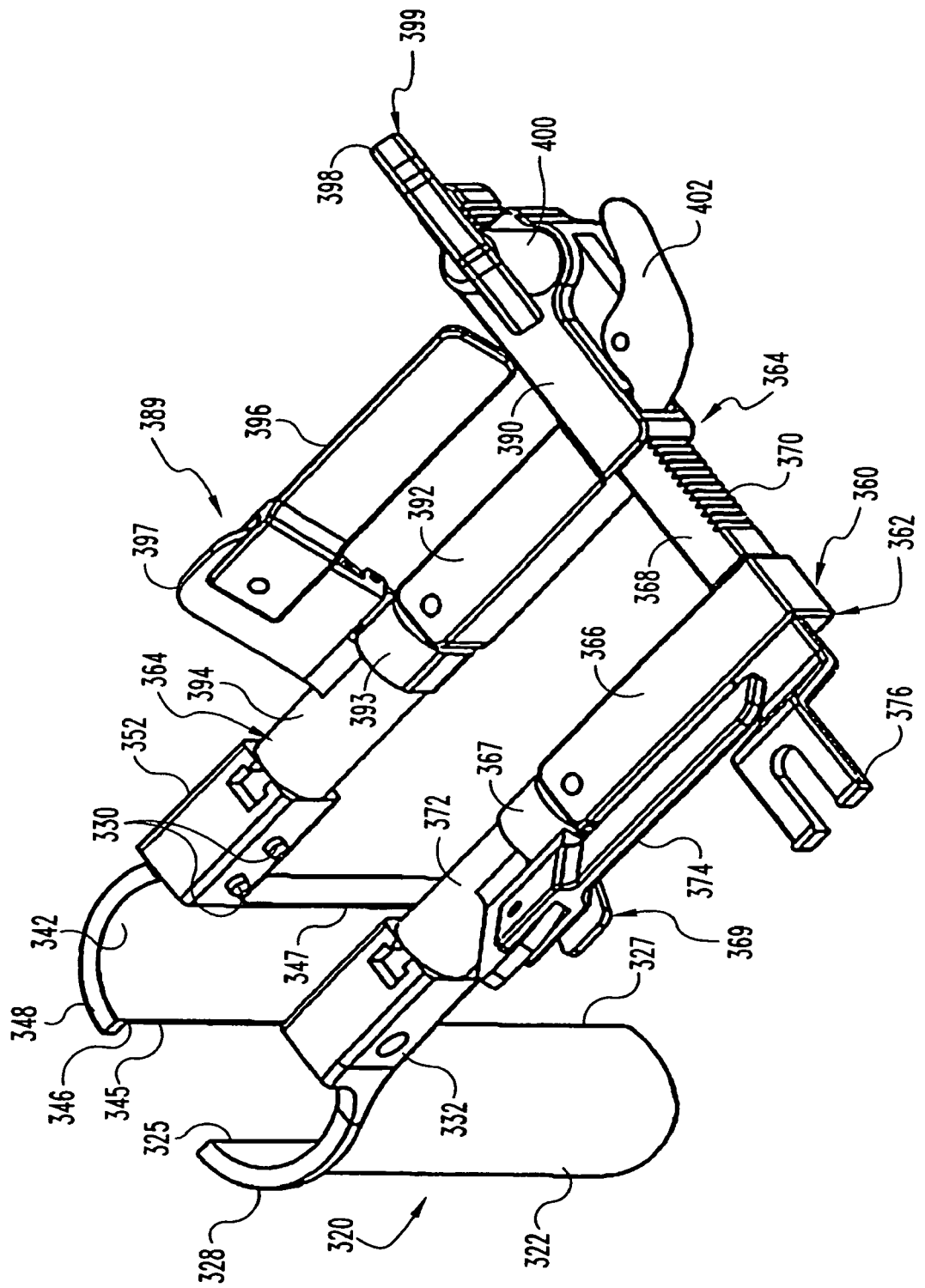
FIG. 19 is another perspective view of the assembly of FIG. 17 with the retractor portions separated.
Figure 20:
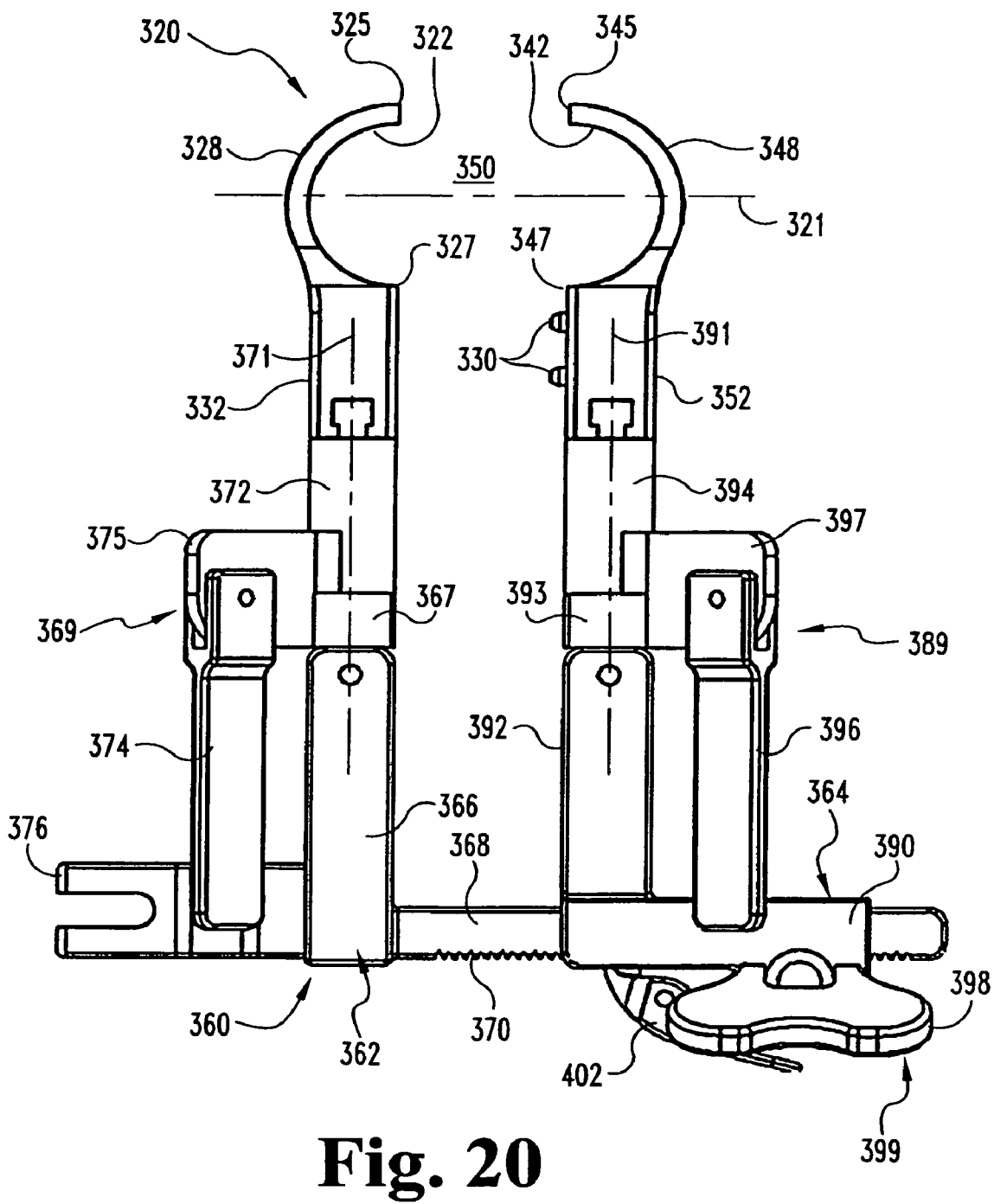
FIG. 20 is a plan view of the assembly of FIG. 19.
Figure 21:
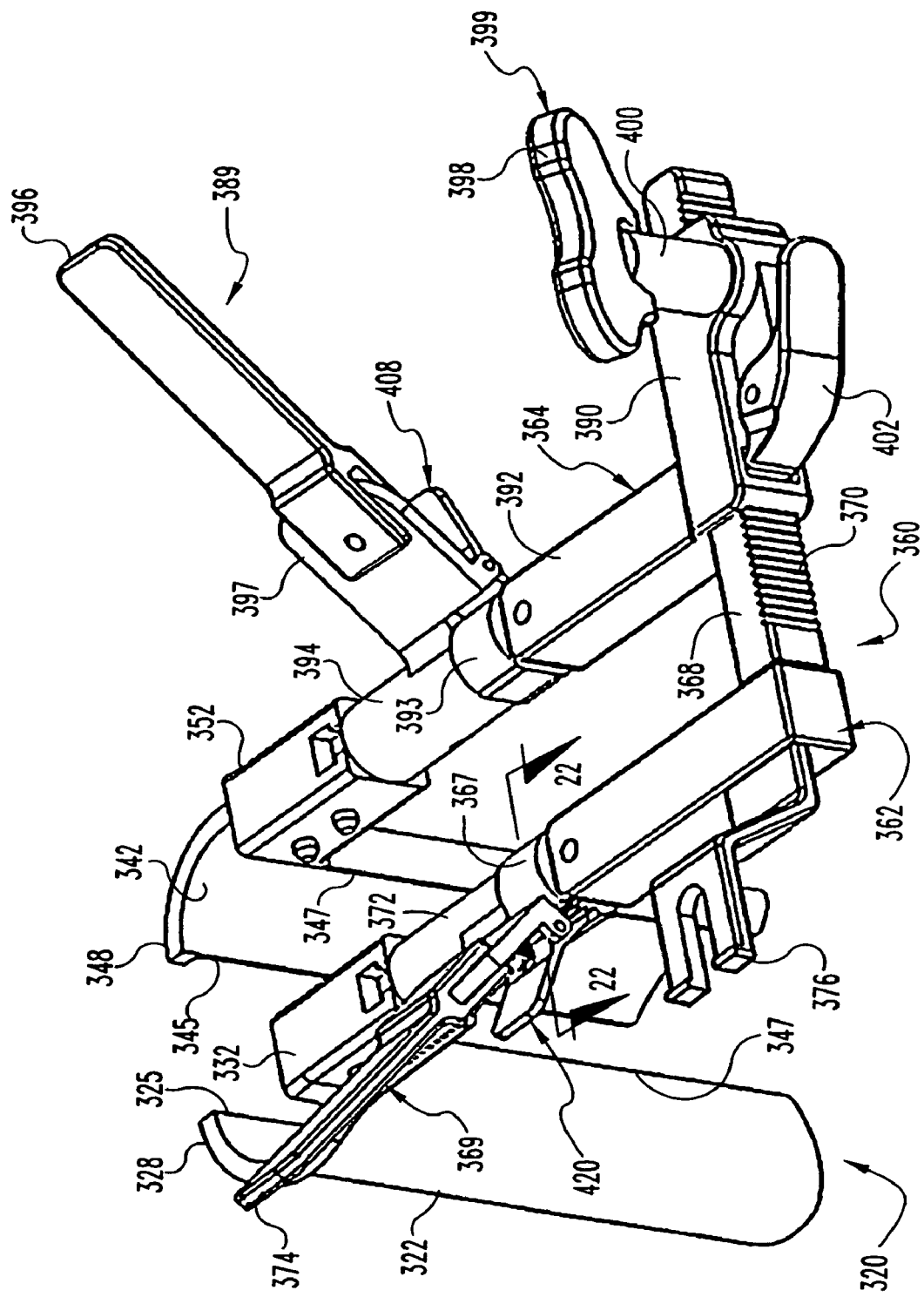
FIG. 21 is a perspective view of the assembly of FIG. 19 with lever arms moved to a pivoting position.
Figure 22:
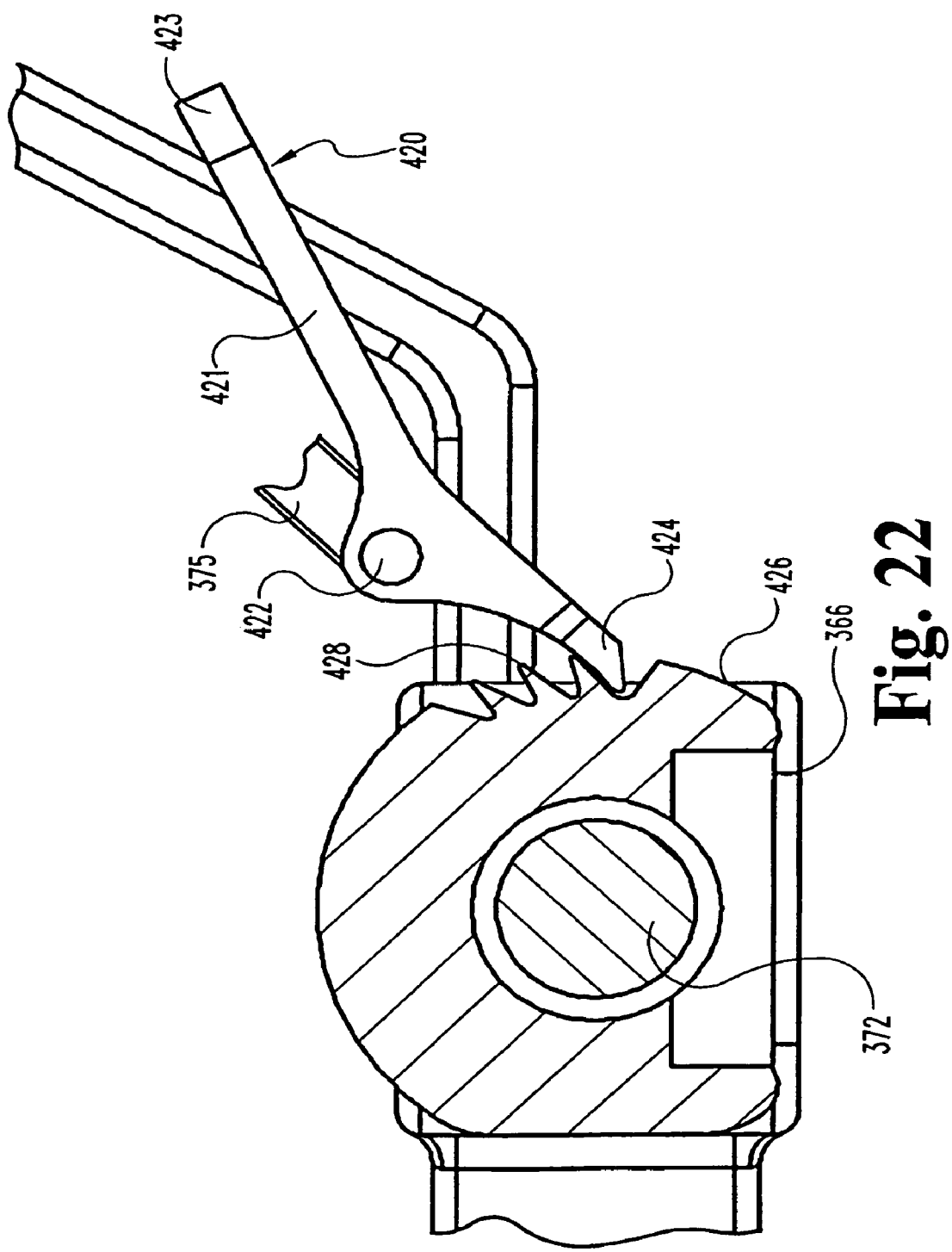
FIG. 22 is a sectional view of a portion of the separation instrument through line 22-22 of FIG. 21 showing a lever arm locking assembly when the retractor portion engaged thereto is in a non-pivoted position.

As shown in FIGS. 19 and 20, alignment members 330 can be provided along one side of one of the engagement structures 332, 352 (engagement structure 352 in the illustrated embodiment.) In the illustrated embodiment, alignment members 330 are rounded protrusions which are received in holes provided in the adjacent side of the other engagement structure 332, 352 when engagement structures 332, 352 are positioned adjacent one another. Alignment members 330 maintain first portion 322 and second portion 342 in longitudinal alignment with one another during and after insertion. Other embodiments contemplate other arrangements for aligning and/or releasably coupling first portion 322 and second portion 342 to one another. Examples of such arrangements include dovetail connections, fasteners, threaded coupling members, clamping members, snap rings, compression bands, straps, ball-detent mechanisms, and releasably interlocking cams or tabs, for example.

Referring to FIGS. 17-20, there is shown a separation instrument 360 operable to move first and second portions 322, 342 away from one another to enlarge working channel 350. It is contemplated that separation instrument 360 includes a lateral separator operable to linearly move first and second retractor portions away from one another along axis 321. It is further contemplated that separation instrument 360 includes at least one rotational separator to pivotally move distal ends of first and second portions 322, 342 away from one another along axis 321. The lateral and rotational separators can be selectively employed by the surgeon during the surgical procedure to enlarge working channel 350 and provide the tissue retraction desired for conducting the surgical procedure through working channel 350. Enlargement of working channel 350 can further retract tissue away from the surgical site distal of the distal ends of retractor portions 322, 342 to provide greater access to tissue, bony structures, and other anatomical spaces located distally of retractor 320.

Separation instrument 360 includes a first connection assembly 362 movably coupled with a second connection assembly 364. First connection assembly 362 is further coupled to first portion 322, and second connection assembly 364 is coupled to second portion 342. First and second connection assemblies 362, 264 extend away from first and second portions 322, 342 and away from the proximal end opening of working channel 350 to facilitate access to working channel 350 during the surgical procedure. First and second connection assemblies 362, 364 are operable to move first and second portions 322, 342 toward and away from one another to separate tissue. First and second connection assemblies 362, 364 further include lever assemblies 369, 389, respectively, that are operable to rotate first and second portions 322, 342 about their proximal ends to move their distal ends away from one another.

Figure 17:
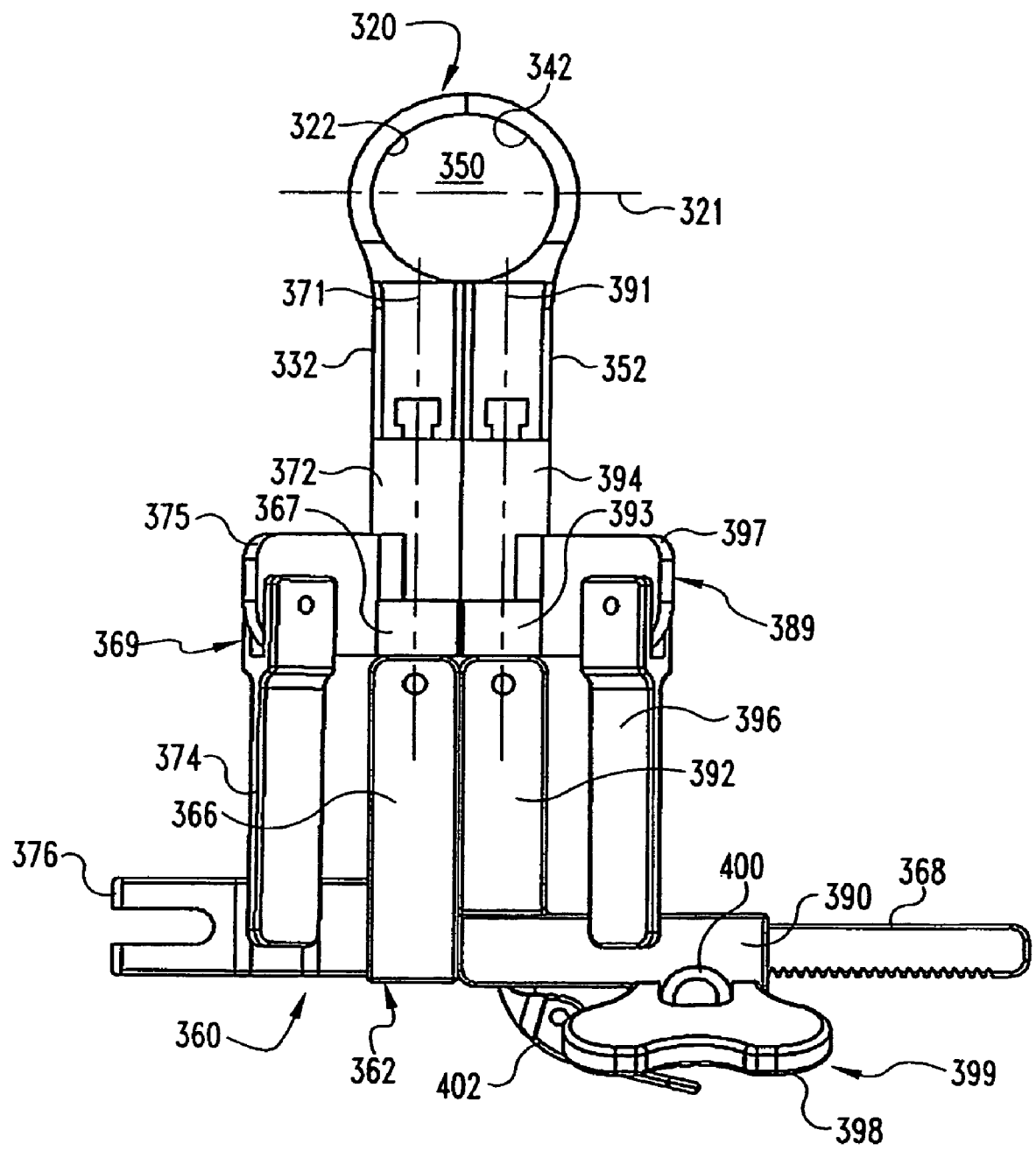
FIG. 17 is a plan view of the retractor of FIG. 15 with a separation instrument engaged.
Figure 18:
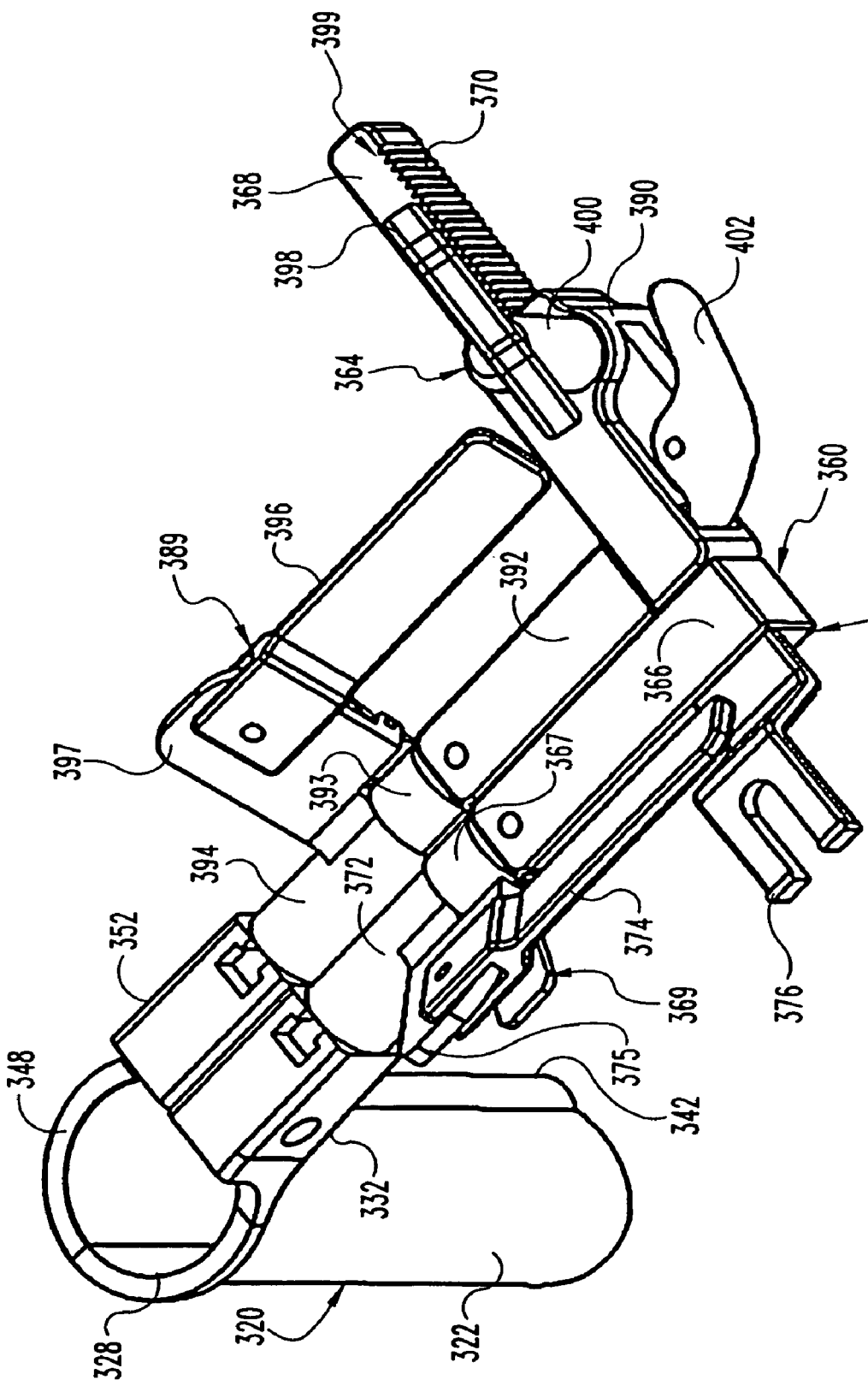
FIG. 18 is a perspective view of the assembly of FIG. 17.

First connection assembly 362 includes a first engagement arm 372 coupled to first engagement structure 332 of first portion 322 and a first extension arm 366 extending from first engagement arm 372. A coupling arm 368 is transversely oriented to and extends from the end of first extension arm 366 opposite first engagement arm 372. A bracket member 376 extends from coupling arm 368, and is engageable by a flexible arm mounted to a surgical table, for example. First connection assembly 362 further includes a first intermediate member 367 fixedly coupled to first extension arm 366. First engagement arm 372 is rotatable relative to intermediate member 367. A first mounting member 375 extends from first engagement arm 372. A first lever arm 374 is pivotally mounted to first mounting member 375 and is movable between a locking position, such as shown in FIG. 17, to a pivoting position, as shown FIG. 21.

Similarly, second connection assembly 364 includes a second engagement arm 394 coupled to second engagement structure 352 of second portion 342 and a second extension arm 392 extending from second engagement arm 394. A housing 390 extends from the end of second extension arm 392 opposite second engagement arm 394. Housing 390 includes a passage through which coupling arm 368 is movably received. An adjustment mechanism 399 mounted to housing 390 is engageable to coupling arm 368 and operable to translate coupling arm 368 in housing 390 to effect movement of first and second portions 322, 342 toward and away from one another along translation axis 321.

In the illustrated embodiment, coupling arm 368 includes a number of ratchet teeth 370 formed therealong, which are engageable by adjustment mechanism 399. Adjustment mechanism 399 includes a gear wheel 400 with teeth that interdigitate with teeth 370 to effect movement of coupling arm 368 in housing 390 as handle 398 is rotated. A locking mechanism 402 is spring-biased into engagement with teeth 370, and maintains separation of first and second portions 322, 342 when handle 398 is released. Locking mechanism 402 can also be depressed to pivot its engagement end out of engagement with teeth 470 and allow first and second portions 322, 342 to move toward one another.

Second connection assembly 364 further includes a second intermediate member 393 fixedly coupled to second extension arm 392. Second engagement arm 394 is rotatable relative to intermediate member 393. A second mounting member 397 extends from second engagement arm 394 alongside second intermediate member 393. Second lever arm 396 is pivotally mounted to second mounting member 397 and is movable between a locking position, such as shown in FIG. 17, to a pivoting position, as shown FIG. 21. Intermediate members 367, 393 can be provided as separate components, or can be integral with the respective extension arm.

Figure 23:
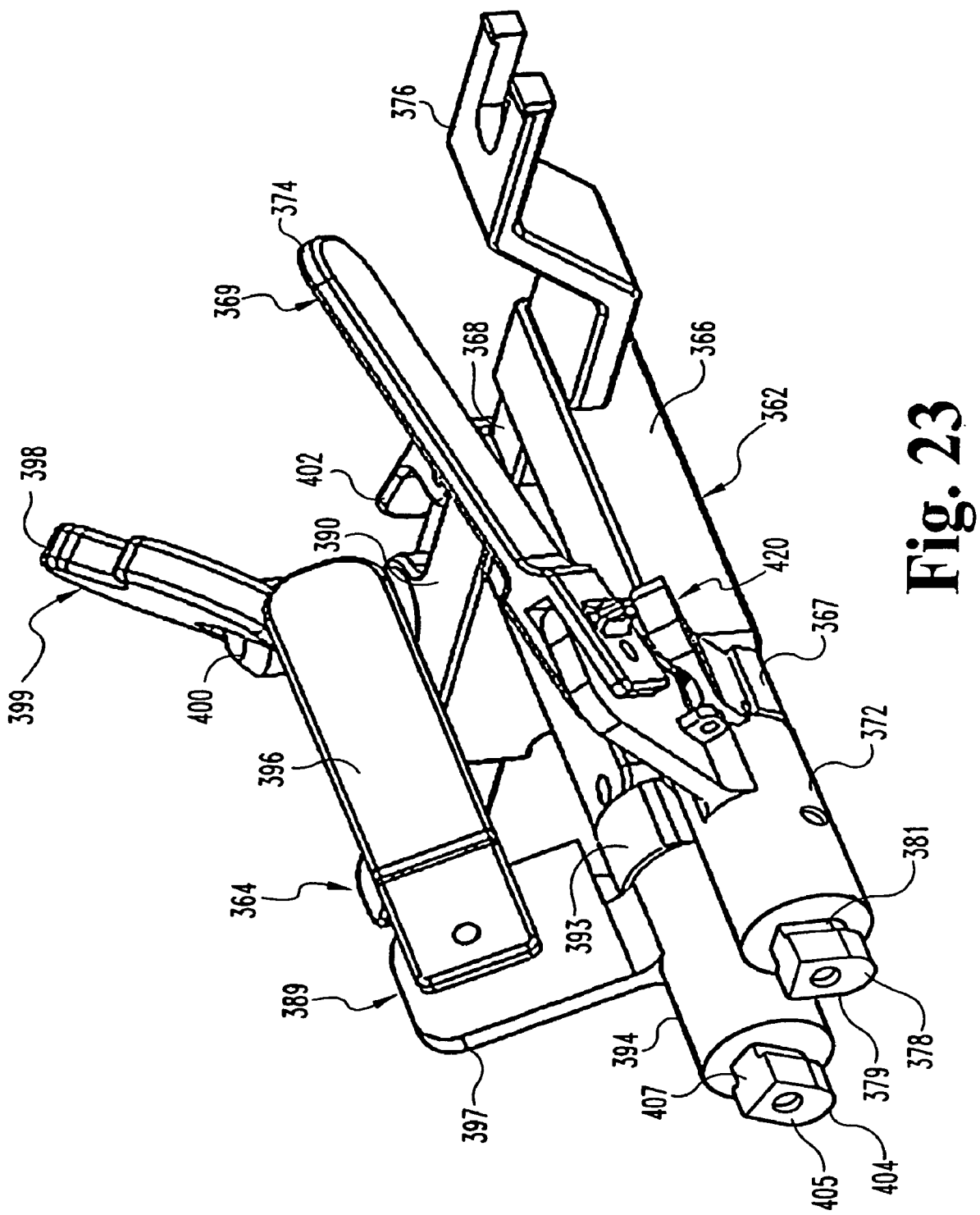
FIG. 23 is perspective view of the separation instrument of FIG. 17 detached from the retractor.
Figure 24:
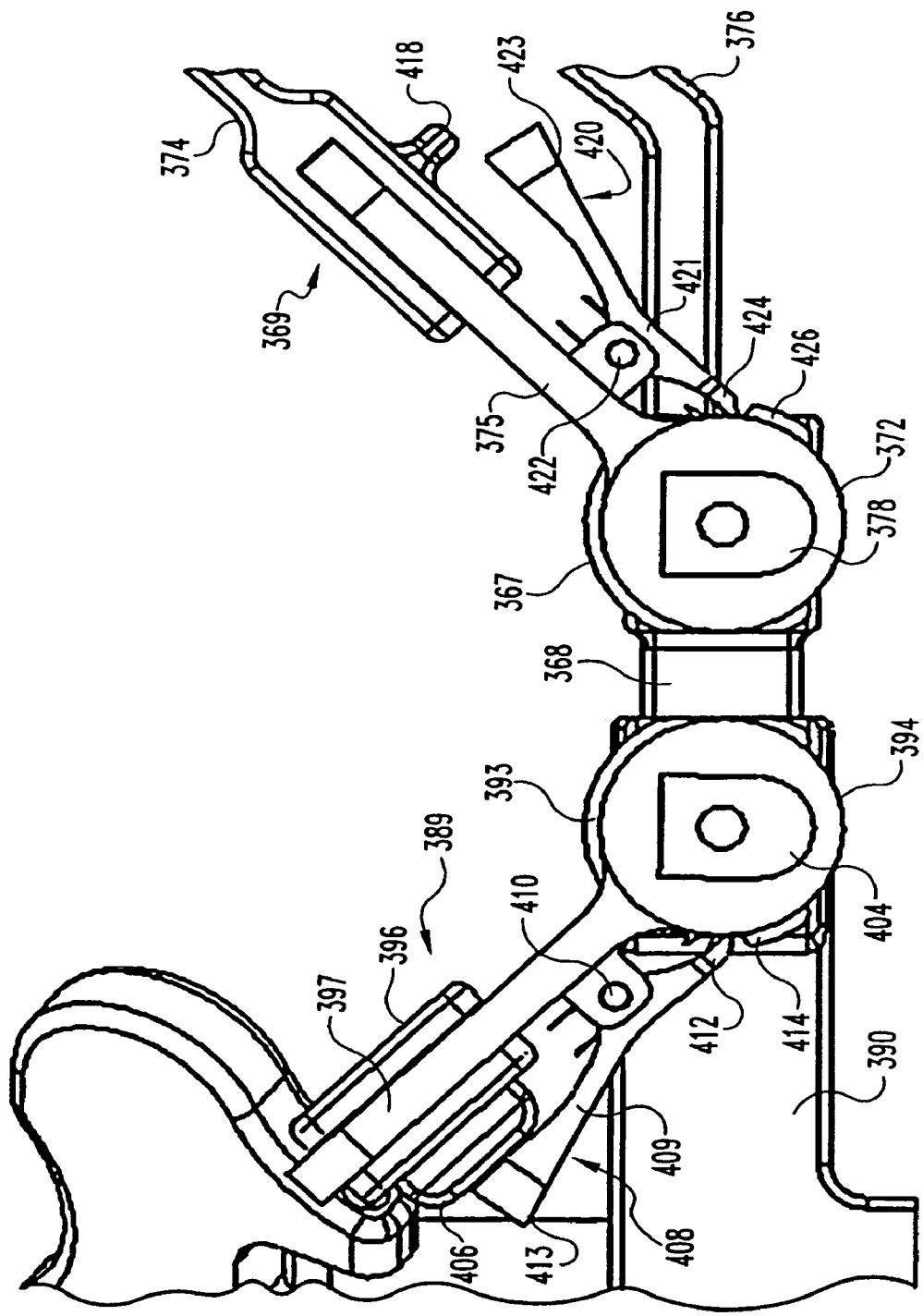
FIG. 24 is an elevation view of a portion of the separation instrument of FIG. 17.
Figure 25:
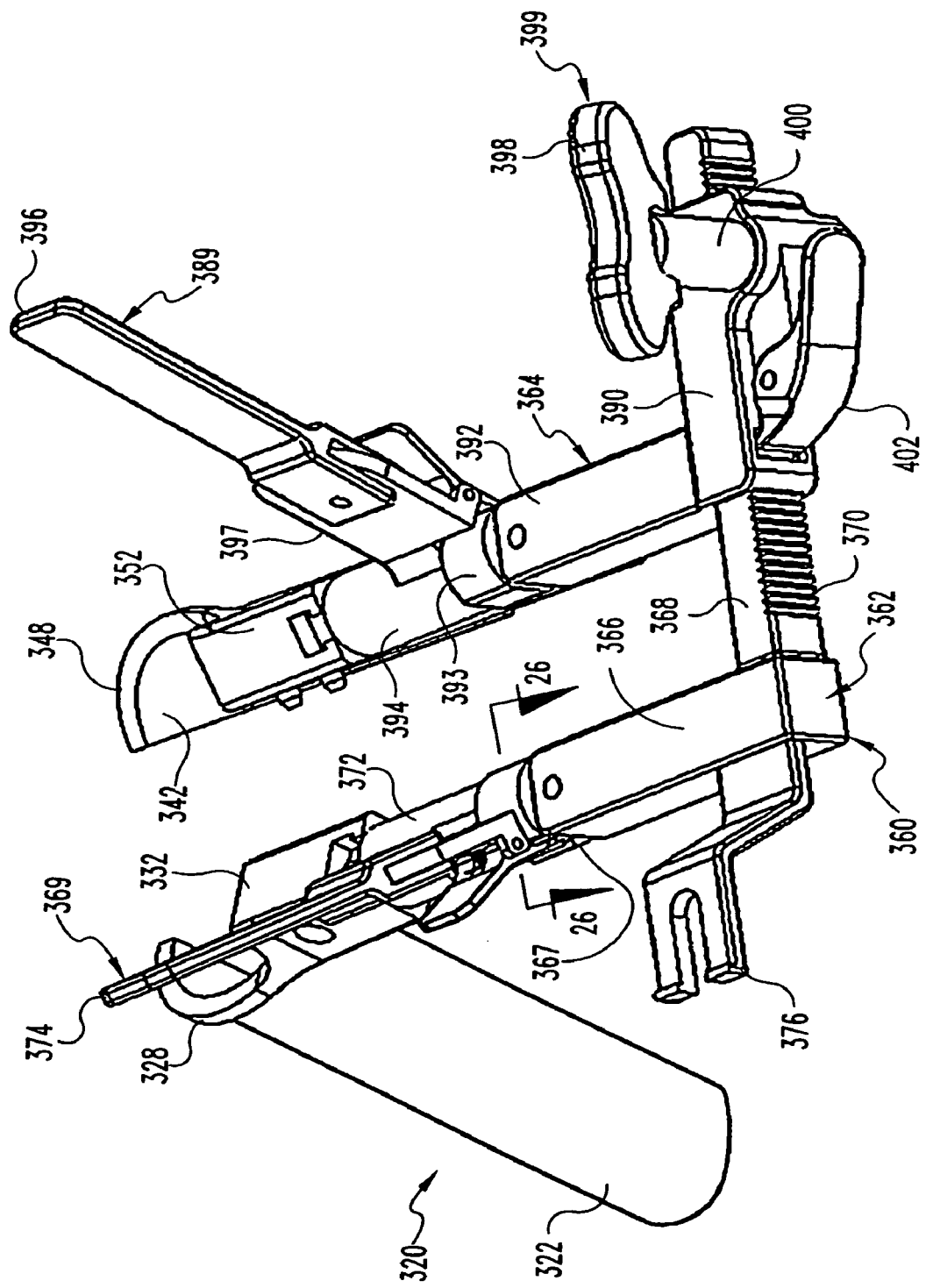
FIG. 25 is a perspective view of the assembly showing the retractor portions pivoted.

As shown in FIGS. 23-24, first and second engagement arms 372, 394 include feet 378, 404, respectively. Feet 378, 404 are slidably and removably received in respective ones of the recesses 333, 353 of engagement structures 332, 352. In the illustrated embodiment, feet 378, 404 include an enlarged outer end portion 379, 405 and a smaller cross-section intermediate transition portion 381, 407 extending between engagement arms 372, 394 and the enlarged outer end portion 379, 405. Intermediate transition portions 381, 407 are received in the intermediate keyway openings 335, 355, and enlarged outer end portions 379, 405 are received in receptacles 337, 357.

Feet 378, 404 are received in recesses 333, 353 (FIG. 15) in such a manner that, as discussed further below, lever arms 374, 396 can effect pivoting of first and second retractor portions 322, 342 by rotating engagement arms 372, 394 about their respective axes 371, 391, respectively. Furthermore, separation instrument 360 can be easily removed from first and second retractor portions 322, 342, facilitating cleanup of the instrument assembly after the surgical procedure. It is also contemplated that disposable first and second portions 322, 342 may be used, or that a set of first and second portions 322, 342 can be provided in various lengths, shapes and/or sizes from which a surgeon may select and employ with separation instrument 360.

Figure 26:
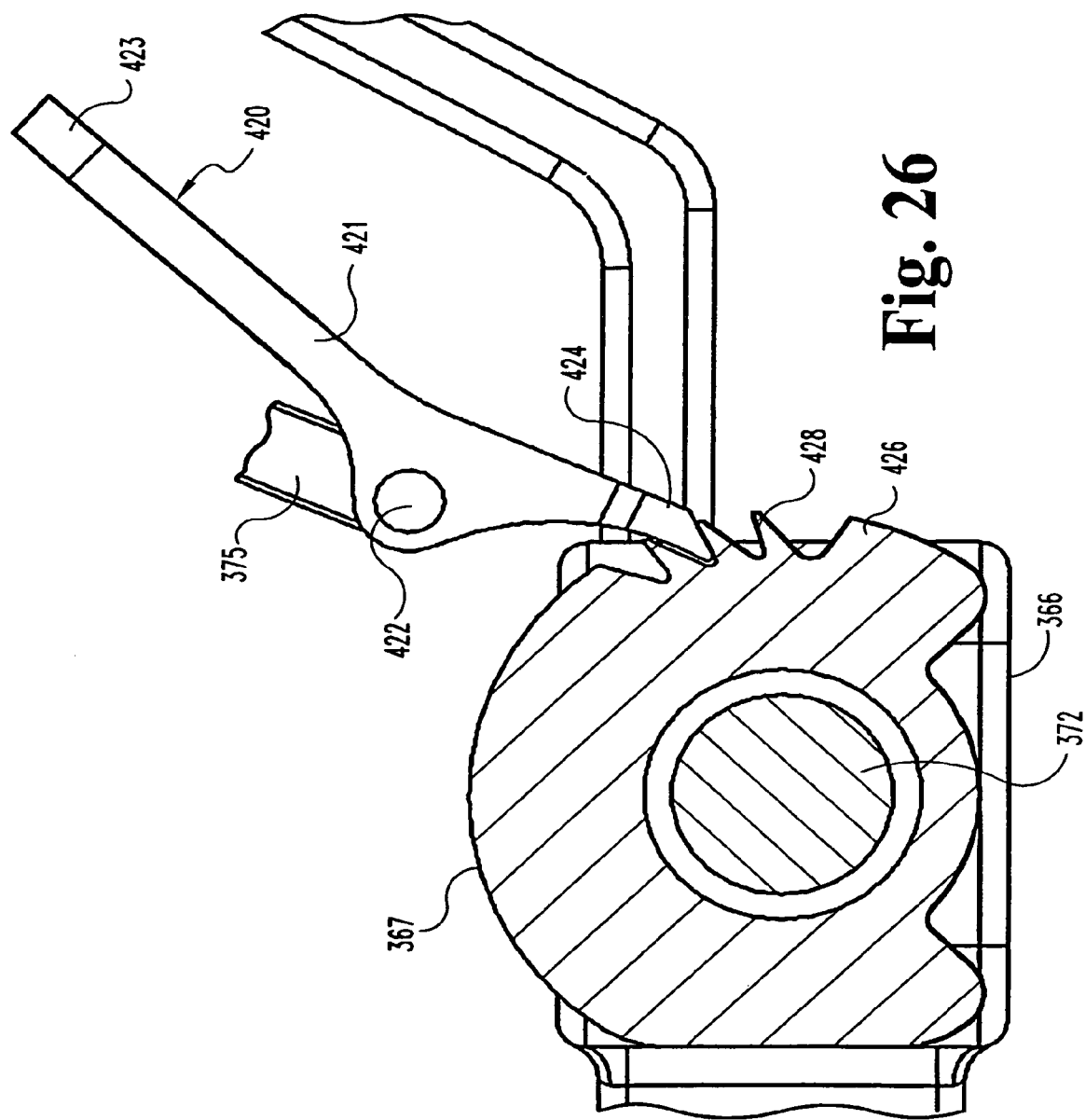
FIG. 26 is a sectional view through line 26-26 of FIG. 25 of a portion of the separation instrument showing the lever arm locking assembly when the retractor portion engaged thereto is in a non-pivoted position.

Intermediate members 367, 393 each include a locking portion, such as engagement portions 426, 414 shown in FIGS. 24, 26, that is engageable with a respective one of the lever arm locking assemblies 420, 408. Lever arm locking assemblies 420, 408 each include a pawl 409, 421 pivotally coupled to an adjacent one of the mounting members 375, 397. For example, as shown in FIGS. 24 and 26, lever arm locking assembly 420 includes a pivot pin 422 mounted to mounting member 375 about which pawl 421 can be pivoted. Similarly, lever arm locking assembly 408 includes a pivot pin 410 mounted to mounting member 397 about which pawl 409 can be pivoted. Intermediate members 367, 393 each include respective ones of engagement portions 426, 414 to which the locking members 420, 408 are engageable to maintain a pivoted position of first and second portions 322, 342.

For example, as shown in FIG. 26 relative to intermediate member 367, there is provided an engagement portion 426 along intermediate member 367 oriented toward pawl 421. Pawl 421 includes a proximal handle portion 423 and a distal engagement end 424. Distal engagement end 424 is positionable in at least one the recesses provided between teeth 428 to maintain a pivoted position of first portion 322. As lever arm 374 is rotated counterclockwise to pivot the distal end of retractor portion 322 away from the distal end of retractor portion 342, pawl 421 moves about engagement portion 426 for engagement there with at a location corresponding to the position of the pivoted retractor portion 322.

Other embodiments contemplate that intermediate members 367, 393 are movable as the respective retractor portion is pivoted. In such embodiments, the pawl 409, 421 does not move or rotate with rotation of engagement arm, but rather remains fixed for engagement with the adjacent engagement portion of the respective intermediate member 367, 393 as it is rotated.

In FIG. 24, first lever arm 374 is shown pivoted on mounting member 375 to its pivoting position, and second lever arm 396 is shown pivoted on mounting member 397 to its locking position. In the locking position, lever arm 396 includes a protrusion 406 that is engageable to the proximal handle portion of pawl 409. In the engaged position, proximal handle portion 413 cannot be moved toward mounting member 397 to remove its engagement end 412 from the teeth along engagement portion 414 of intermediate member 393. Accordingly, the pivoted position of second retractor portion 342 is locked by the positioning of lever arm 396 in its locking position, and second retractor portion 342 cannot be moved unless lever arm 396 is moved to its pivoting position.

In FIG. 24 first lever arm 374 is shown in its pivoting position, and includes a protrusion 418 extending from first lever arm 374 that is positioned out of contact with pawl 421. In this position, pawl 421 can be pivoted about pin 422 to remove engagement end 424 from between teeth 428. Lever arm 374 can then be manipulated to pivot first retractor portion 322 to a desired angular position along axis 321. As lever arm 374 is pivoted, locking member 420 is moved therewith into alignment with another space between teeth 428. When the desired orientation of first portion 322 is obtained, then proximal handle portion 423 can be released, and locking member 420 can be spring biased or otherwise moved to engage engagement portion 426 and maintain the pivoted position of first portion 322. Lever arm 396 can then be pivoted on mounting member 375 to its locking position where protrusion 418 engages pawl 421 to prevent it from being released from engagement portion 426.

Figure 27:
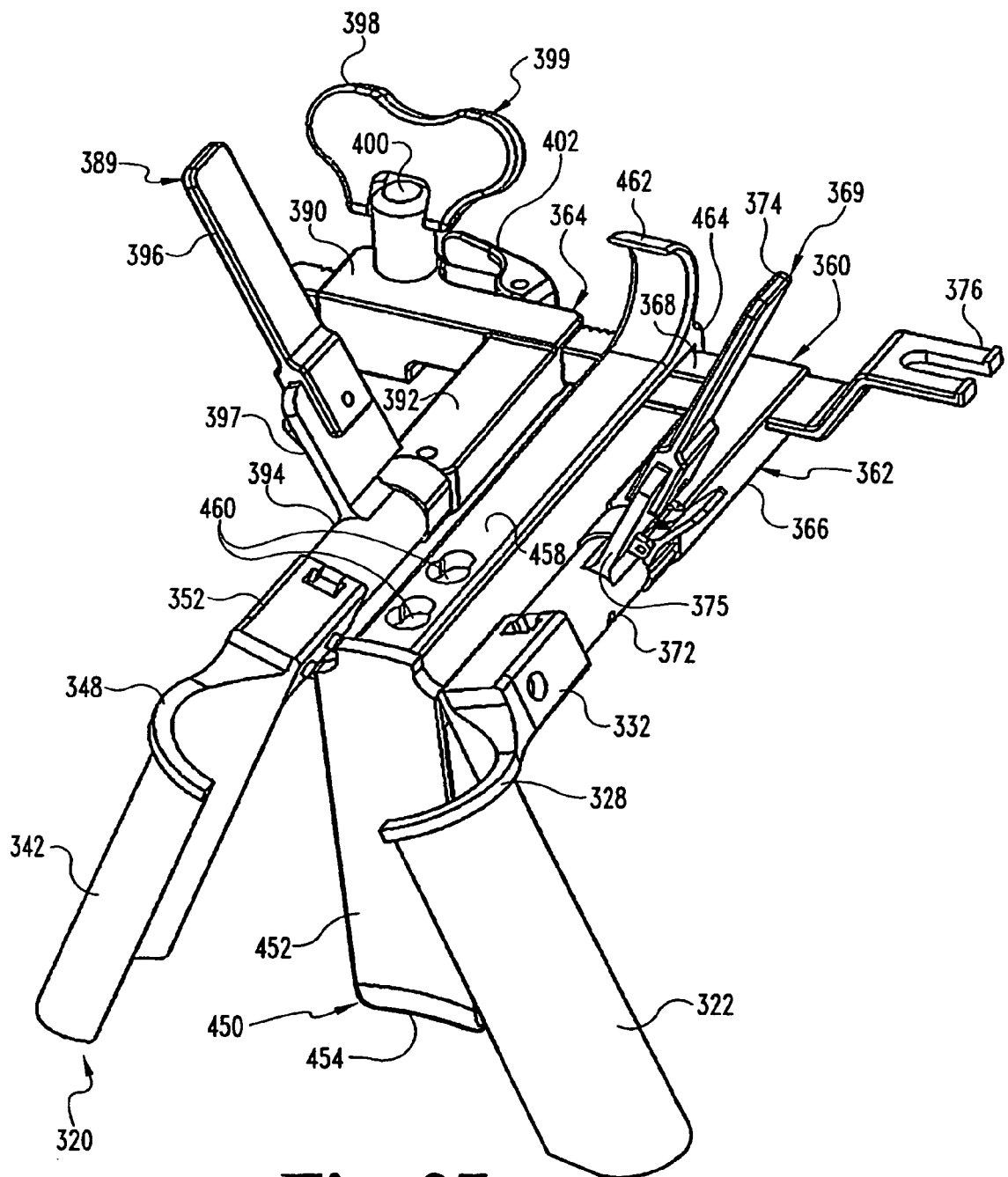
FIG. 27 is a perspective view of the assembly of FIG. 19 showing the retractor portions pivoted and a first intermediate retractor assembly engaged to the separation instrument.
Figure 28:
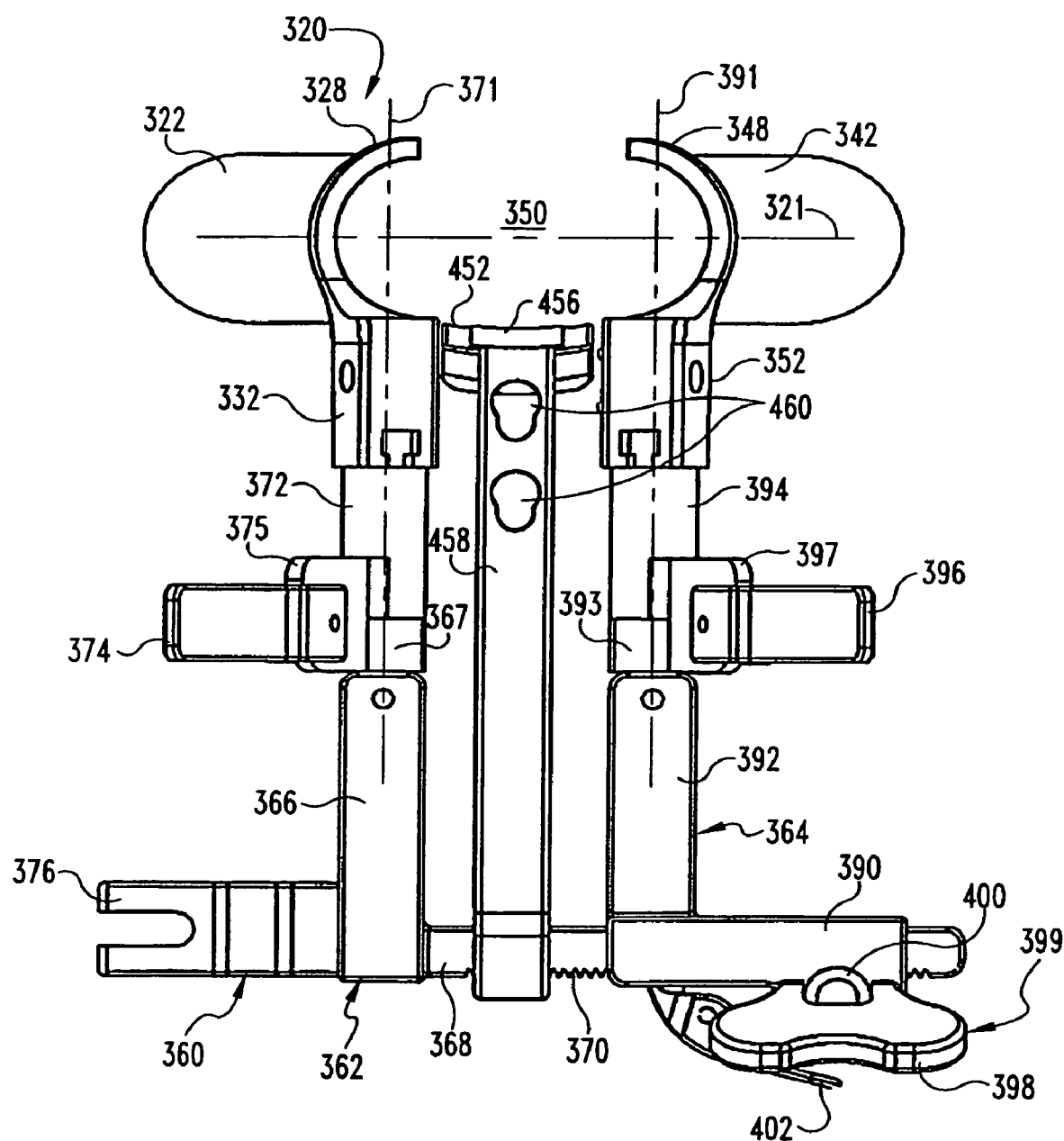
FIG. 28 is a plan view of the assembly of FIG. 27.

Referring to FIGS. 27-28, there is shown a first intermediate retractor assembly 450 engageable to separation instrument 360. Intermediate retractor assembly 450 includes a retractor blade 452 positionable between first and second retractor portions 322, 342 to retract and/or maintain tissue from the working channel 350 in a direction transverse to axis 321. In one operative approach to the spine, retractor 320 is oriented so that retractor portions 322, 342 are movable along axis 321 oriented in the direction of the central axis of the spinal column, and blade 450 is positioned medially or adjacent to the spinal column relative to the other retractor blade portions 322, 342. Other operative orientations in the incisions for the retractor blades and retractor portions are also contemplated.

First intermediate retractor assembly 450 includes blade 452 extending between a distal end 454 and a proximal end 456. As shown in FIG. 28, distal end 454 is curved away from the working channel 350, and can rest upon bone or other tissue when positioned in the retracted incision. Blade 452 can include a flat profile between distal end 454 and proximal end 456, or include a convex curvature about its longitudinal axis or along its longitudinal axis. Blade 452 can also be provided as a single member, or in one or more components movable relative to one another to lengthen or shorten blade 452.

A linking arm 458 is transversely oriented to and extends from proximal end 456 of blade 452. Opposite blade 452 there is provided an engaging portion in the form of first and second hook members 462, 464. Lower hook member 464 can be positioned about coupling arm 368 of separation instrument 360. Linking arm 458 has a length such that the pressure from the tissue at the incision against blade 452 firmly holds hook member 464 against coupling arm 368. Upper hook member 462 can serve as a handle to facilitate placement of lower hook member over coupling arm 368 or removal of intermediate retractor assembly 450. Other arrangements for securing blade 452 to coupling arm 368 are also contemplated, such as fasteners and interfitting components, for example.

Figure 29:
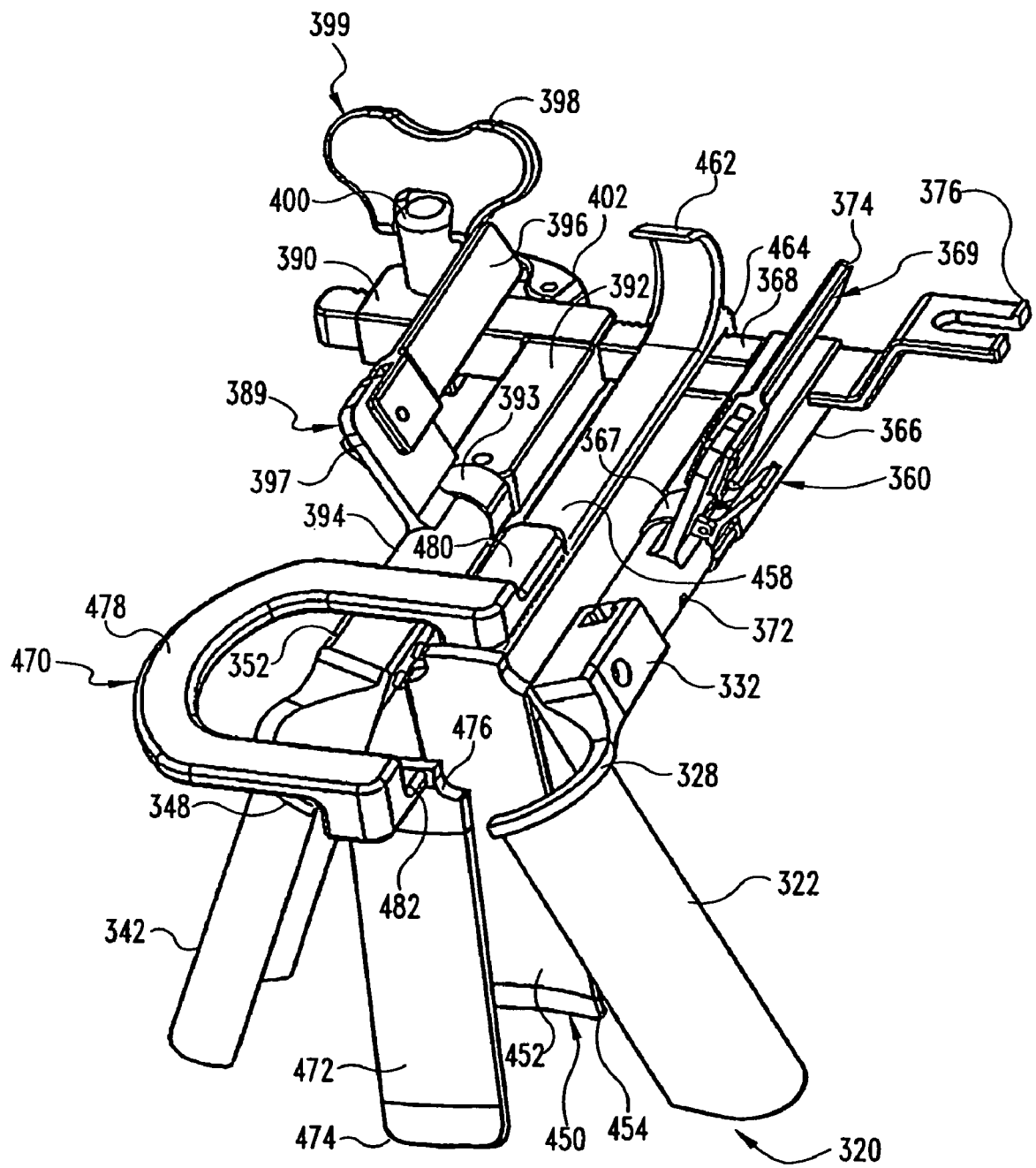
FIG. 29 is a perspective view of the assembly of FIG. 27 with a second intermediate retractor assembly engaged to the first intermediate retractor assembly.
Figure 30:
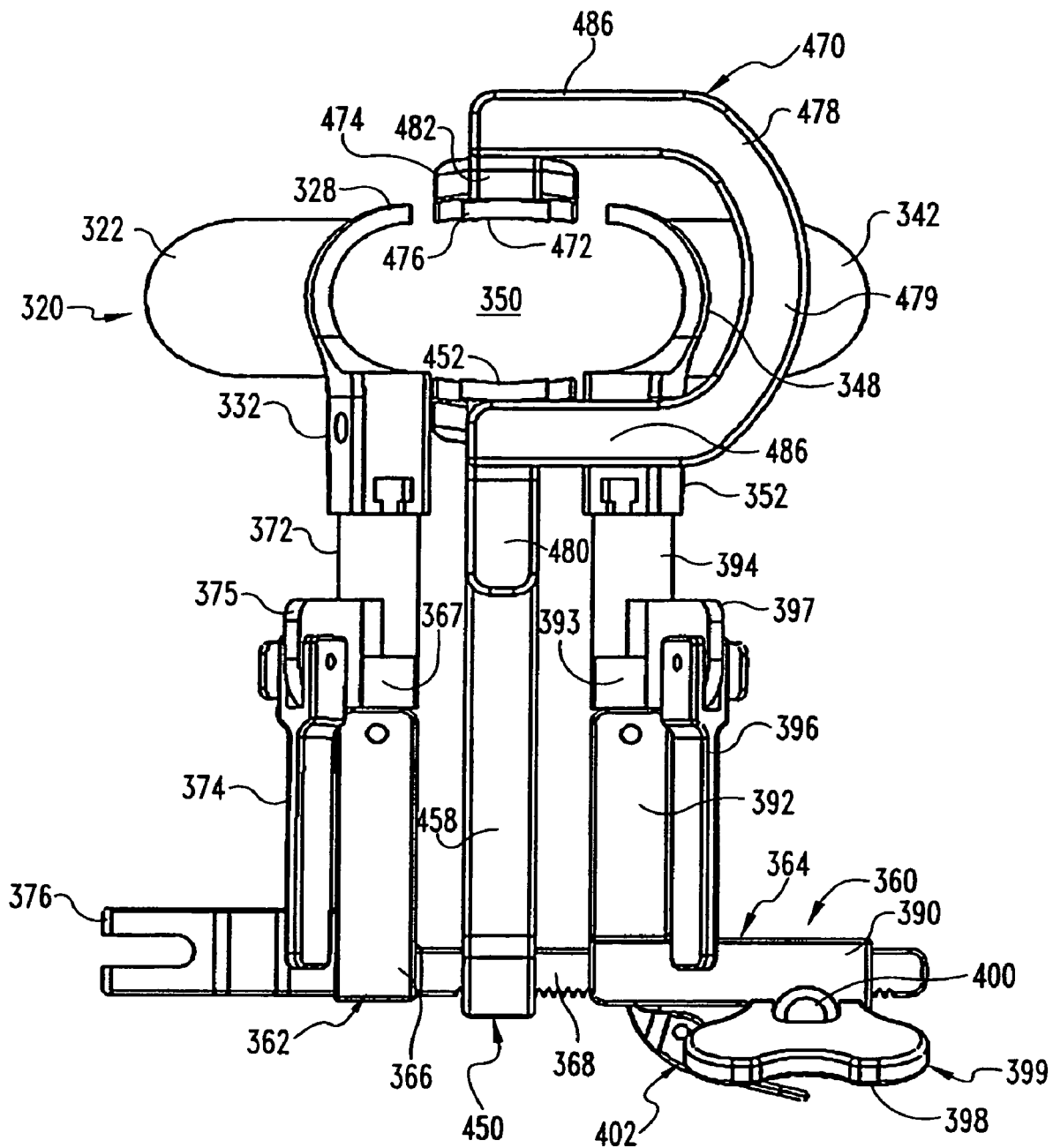
FIG. 30 is a plan view of the assembly of FIG. 29.

First intermediate retractor assembly 450 is further mountable by a second intermediate retractor assembly 470, as shown in FIGS. 29 and 30. Second intermediate retractor assembly 470 includes a blade 472 extending between a distal end 474 and a proximal end 476. Distal end 474 and the blade portion extending therefrom can be configured as discussed above with respect to blade 452. A second linking arm 478 extends from proximal end 476, and includes an engagement foot 480 opposite blade 472. Engagement foot 480 is removably mountable to linking arm 458 of first intermediate retractor assembly 450.

First linking arm 458 includes slotted holes 460 (FIGS. 27-28) extending therethrough adapted to receive pins (not shown) extending from a lower surface of foot 480 of second linking arm 478. The pins can be provided with enlarged heads positionable in the enlarged portions of slotted holes 460, and are slidable to the narrowed ends of the slotted holes 460 so that the heads are captured in slotted holes 460. In the illustrated embodiment, the narrowed portions of the slotted holes 460 extend opposite retractor blade 472 so that the pressure from the tissue about the incision pushing against blade 472 maintains the pins of foot 480 in the narrowed end portions of slotted holes 460.

Second linking arm 478 includes offset portions 486 extending transversely to first linking arm 458. Offset portions 486 are linked by an offset member 479 extending therebetween. Offset member 479 can be provided with an arcuate profile to extend around the respective adjacent retractor portion 322, 342 so as to not obstruct access to working channel 350. Retractor blade 472 can maintain tissue retraction and provide protection to tissue located along the side of the working channel opposite retractor blade 452. First and second intermediate retractor assemblies 450, 470 provide the surgeon with additional options during the surgical procedure with regard to tissue retraction and protection that can be readily employed with separation instrument 360 engaged to retractor 320.

In one surgical procedure, retractor 320 is engaged to separation instrument 360 and inserted in an incision. Retractor 320 can be advanced over one or more dilators dilating an incision, or directly into the incision. Separation instrument 360 is then operated to linearly move retractor portions 322, 342 away from one another along axis 321 to enlarge working channel 350. One or both of the lever arms 374, 396 can be moved to its pivoting position and manipulated to pivot the respective retractor portion 322, 342. When the retractor portion has been pivoted, the respective lever arms are moved to their locking position so that the protrusion extending therefrom engages the adjacent pawl 409, 421 to maintain the pawl in engagement with adjacent engagement portion 414, 426.

When the desired separation has been obtained, the surgeon has the option to select first intermediate retractor assembly 450. Blade 452 is positioned in the incision between the separated first and second retractor portions 322, 342, and linking arm 458 is secured to coupling arm 368. The surgeon has the further option of selecting second intermediate retractor assembly 470, and positioning blade 472 in the incision opposite blade 452. Linking arm 478 can then be secured to linking arm 458. Further adjustment of the spacing and orientation of retractor portions 322, 342 can be completed with separation instrument 360 and/or lever arms 374, 396.

It is further contemplated that retractor portions 322, 342 need not be separated from one another linearly, but are separated during the surgical procedure only by pivoting one or both of them along axis 321. Once the working channel 350 provides the desired access, the surgeon can remove bone, tissue, disc material, or other matter through retractor 320. Implants, such as fusion devices, screws, plates, rods, artificial discs, bone growth material, and other repair devices or therapeutic substances can be delivered through retractor 320 to the desired site in the patient's body.

The system may also include a dilator configured to increase the size of the incision prior to positioning of the access portal in the incision. The dilator may include a set of dilators as illustrated in FIGS. 14a-f. A procedure that includes a use of dilators and other associated equipment is described in the illustrated example.

The present embodiment permits a substantially lateral approach to the spine. It is understood that many aspects of the procedure can be performed from other approaches to the spine, such as postero-lateral, mid-line or medial posterior, and anterior. A guidewire 150 can be advanced through the skin and tissue into a disc space or vertebral body V. A small incision may be made in the skin to facilitate penetration of the guidewire through the skin. In addition, the guidewire, which may be a K-wire, may be inserted under radiographic or image guided control to verify its proper positioning. It is, of course, understood that the guidewire 150 can be positioned at virtually any location in the spine and in any portion of a vertebra V.

Figure 14A:
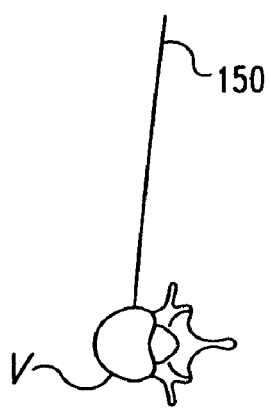
FIGS. 14a-f are partial cross-section and side elevation views of embodiments of the invention applied to a spinal column.
Figure 14B:
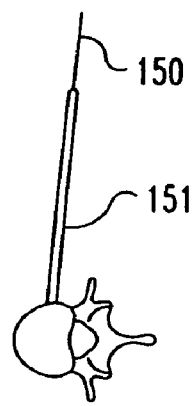
Figure 14C:
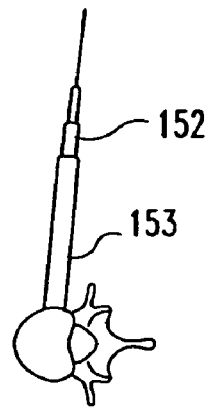
Figure 14D:
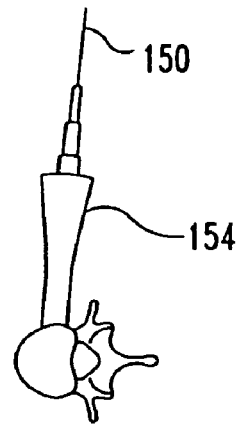
Figure 14E:
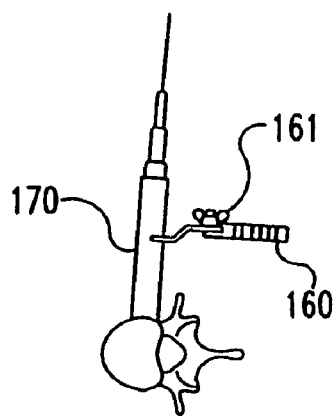
Figure 14F:
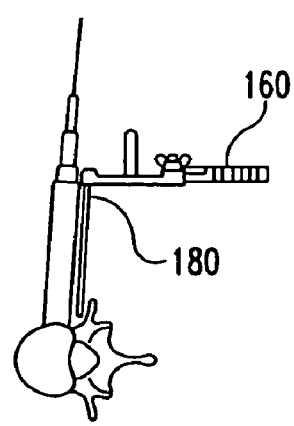

One or more tissue dilators may then be advanced over the guidewire 150, as depicted in FIGS. 14b and 14c. Alternatively, the dilators can be advanced through the incision without the aid of a guidewire, followed by blunt dissection of the underlying tissues. In the specific illustrated embodiment, a series of successively larger dilators 151, 152 and 153 are concentrically disposed over each other and over the guidewire 150 and advanced into the body to sequentially dilate the soft tissues. In a specific embodiment, the dilators have successively larger diameters, ranging from 5 mm, to 9 mm to 12.5 mm for the largest dilator. Other dilator sizes are contemplated depending upon the anatomical approach and upon the desired size of the working channel.

In an embodiment of the invention, an over-dilator 154 (FIG. 14d) is used in a final dilation step to provide additional dilation of the tissues furthest from the surgical site without substantially increasing the dilation of the tissues adjacent to the surgical site. Such retraction may be useful to enhance visualization of the surgical site and to provide additional space to angulate and operated instrumentation without increasing manipulation of neural and vascular structures near the surgical site. In some embodiments, the over-dilator 154 could remain in place as an access portal. In some embodiments, the over-dilator 154 is designed to prepare tissues for an additional tubular port, a retractor, or some other structure for creating an access portal. The over-dilator 154 illustrated fits concentrically over smaller dilators 150-153, and has a proximal end that is larger than its distal end. The illustrated device has a circular cross-section, but any functional cross-section or combination of cross-sections is contemplated.

As shown in FIG. 14e, the tubular port 170 is advanced over the largest dilator 153. The dilators and guidewire 150 may then be removed, leaving in place the tubular port 170 to serve as an access portal. Similarly, as illustrated in FIG. 14f, the retractor 180 is advanced over the largest dilator 153. The dilators and guidewire 150 may then be removed, leaving in place the tubular port 170 to serve as an access portal.

With an access portal established, a working channel is formed between the skin of the patient and a working space adjacent the spine. It is understood that the length of the access portal is determined by the particular surgical operation being performed and the anatomy surrounding the working space.

In some embodiments, the tubular port 170 or retractor 180 are at least initially only supported by the soft tissue and skin of the patient. However, both the tubular port 170 and the retractor 180 include mounting structures for fastening to a flexible support arm 160, which can be of known design. The flexible support arm 160 may be mounted to the tubular port 170 or the retractor 180 by way of a bolt and wing nut 161, as shown in FIGS. 14e and 14f, although other fasteners are also contemplated. This flexible arm 160 can be mounted on the surgical table and can be readily adjusted into a fixed position to provide firm support for the access portal. The flexible arm 160 is configurable so that it can be contoured as required to stay clear of the surgical site and to allow the surgeons adequate room to manipulate the variety of tools that would be used throughout the procedure. Various visualization and illumination devices may also be attached to the tubular port 170 and the retractor 180 to provide better access to the surgical site as desired by the surgeon. Examples include but are not limited to, fiber optic lighting, visualization tubes, endoscopes, microscopes and the like.

There is further contemplated an instrument set having two or more self-distracting trial instruments and at least one implant. The two or more trial instruments each have a body with a leading insertion end sized for insertion into a collapsed disc space. The leading insertion ends of each trial instrument are substantially the same in size and shape. Each trial instrument has a height proximal the leading insertion end that restores the collapsed disc space height to a height different than that of the other trial bodies. The at least one implant has a leading insertion end that is substantially the same in size and shape as the leading insertion end of at least one of the trial bodies of the trial instruments. The implant has a height proximal its leading insertion end that corresponds to the desired restored disc space height provided by the at least one trial instrument.

Also contemplated is a kit including a set of trial instruments, each having a trial instrument at a distal end thereof. The trial bodies have a self-distracting leading end portion insertable in a collapsed spinal disc space. The kit further includes a set of implants positionable in the collapsed spinal disc space. Each implant has a body sized and shaped to correspond in size and shape to a respective trial instrument. The fit of each implant body in the spinal disc space is indicated to the surgeon by the fit of the corresponding trial instrument. When a trial instrument provides a desired fit, the trial instrument is removed and the implant corresponding to the trial instrument is inserted into the collapsed disc space in the location previously occupied by the withdrawn trial instrument.

Figure 31A:
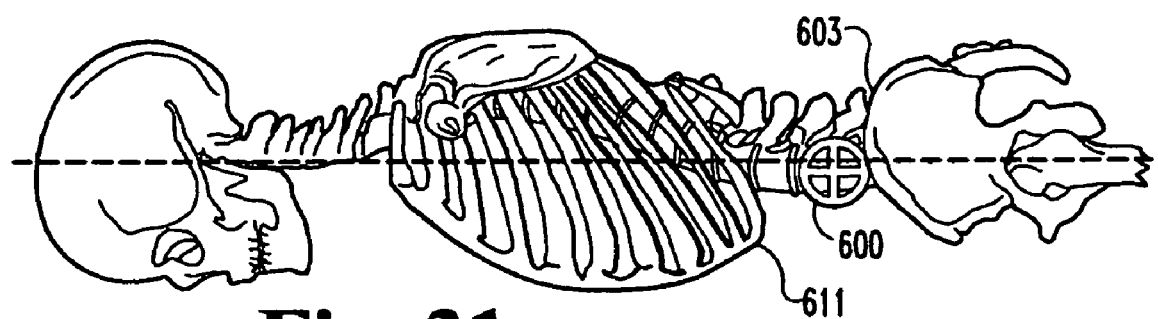
FIG. 31a is an elevation view along the coronal plane of a human skeleton.
Figure 31B:
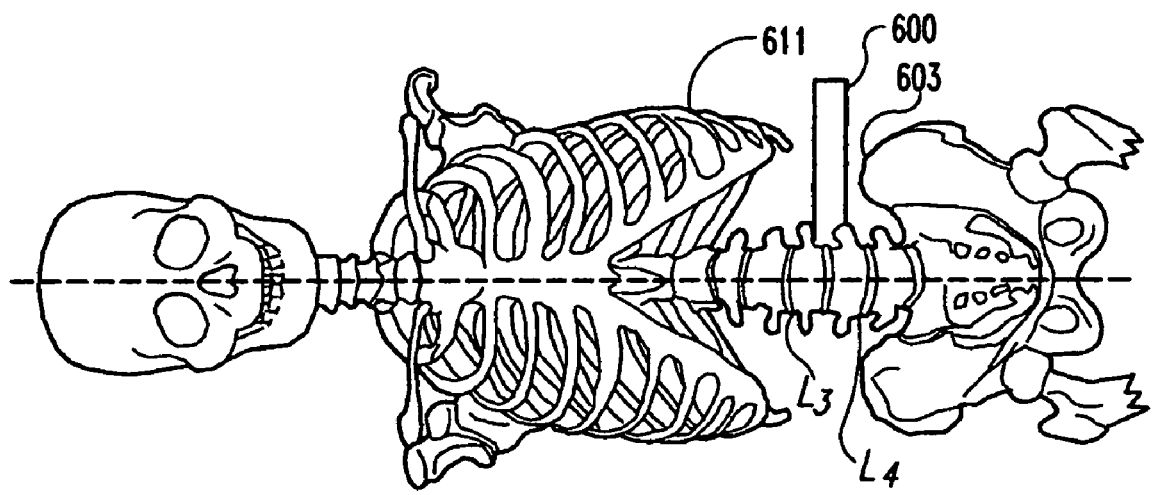
FIG. 31b is an elevation view along the sagittal plane of a human skeleton.
Figure 32:
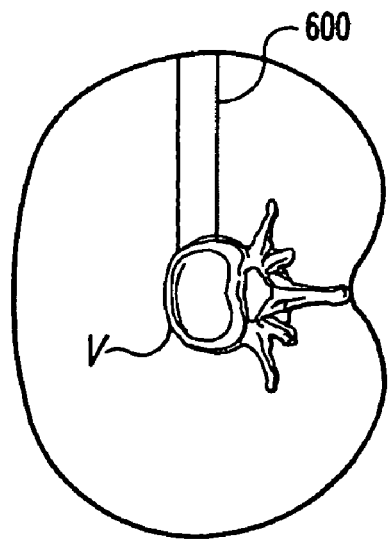
FIG. 32 is a cross-sectional view through the lumbar region of a human.

Referring to FIGS. 31a, 31b, and 32, elevation views along the coronal plane and the sagittal plane, respectively, of a human skeleton are presented. FIG. 32 shows a cross-sectional view through the lumbar region of a human. A lateral surgical approach vector 600 terminating between lumbar vertebral bodies L3 and L4 is illustrated. A ribcage 611 and an iliac 603 of the skeleton are shown on either side of the approach vector 600.

Method embodiments of the invention include surgically placing an implant between vertebral bodies from a generally lateral surgical approach. One generally lateral surgical approach is illustrated by lateral surgical approach vector 600. Variations of the lateral approach include, without limitation, posteriorly oblique and anteriorly oblique deviations as well as deviations along the coronal plane. A deviation in the coronal plane, including "tilting" the approach such that the approach is not perpendicular to the longitudinal axis of the spine, may be necessary to reach various spinal discs and/or to avoid certain skeletal and soft tissues of patient.

A patient would be positioned such that an operative side of the patient is accessible. A patient may be placed on their side, back, or stomach to make such an access. The table or other structure on which the patient is placed may be tilted in any plane or elevated to provide access. In some situations, it is desirable to place a protrusion against a non-operative side of the patient to cause separation between the ribcage 611 and the iliac crest 603 of the patient on the operative side. In effect, the patient is "bent around" the protrusion to open up the operative side in such embodiments. An incision is made in the operative side of the patient between the ribcage 611 and the iliac 603. An incision may be made with any effective device, including by insertion of an initial insertion dilator. The initial insertion dilator may be a guidewire 150 (FIGS. 14a-f). An initial insertion dilator is located between the vertebral bodies in an embodiment of the invention. In other embodiments, the initial insertion dilator could be located in one of the vertebral bodies or some other tissue region. Tissue may be dilated with a first concentric dilator that fits over the initial insertion dilator to further open the incision. Variations of this procedure and additional effective procedures are described in association with FIGS. 14a-f.

Embodiments of the invention include inserting a tubular port 170 (FIG. 14e) or a retractor structure 180 into the incision (FIG. 140. The tubular port 170 or the retractor structure 180 provide an access portal to the surgical site. In some embodiments, the insertion of the tubular port 170 or the retractor structure 180 includes insertion over one or more dilators. Operation of the retractor structure 180 may be accomplished to further open the incision. Operation of the retractor structure 180 is described extensively in association with FIGS. 15-30. In some embodiments, parts of the retractor structure 180 may be attached to one or more vertebral bodies with a fastener or other effective device. Such attachment may assist with the application of retraction forces between vertebral bodies and/or may stabilize the relative positioning of retractor structure 180 and the anatomy.

Removal of vertebral disc material to create an opening for the implant between the vertebral bodies may be accomplished with any tool capable removing disc material. In some embodiments at least one of a pituitary rongeur, a rotary shaver, a rasp, and a scraper are used. Such instruments may be hand operated or driven by a power source. According to one method, the collapsed disc space is accessed, and an opening is formed in the annulus having a width corresponding to the width of the trial bodies and/or implants. Disc material is removed through the annulus opening, and, if desired by the surgeon, manual roughening of the endplates is performed with a scraper or other suitable endplate roughening instrument.

In some embodiments, a trial instrument is inserted between the vertebral bodies. The function of the trial may be to evaluate the size of the disc space or to distract the height of the disc space. A surgeon can also determine whether a trial instrument or implant provides a desired disc space height by tactile feedback of the inserted trial instrument or implant, and also by visual inspection. It may be desirable for the inserted trial instrument or implant body to sufficiently stretch the remaining annulus tissue to provide firm engagement between the upper and lower surfaces of the trial or implant body and the adjacent vertebral endplates. Sufficient surface area contact may be desirable to prevent or minimize post-operative movement of the adjacent vertebrae relative to the implant. By providing trial bodies and implant bodies of corresponding size and shape, and by inserting the trial bodies and implant bodies in a non-distracted disc space, the inserted trial or implant body may provide immediate feedback to the surgeon of the desirability of the fit. If distraction were maintained by, for example, a second distractor, feedback to the surgeon of the post-operative fit of the implant would not be reliable or available, if at all, until distraction were removed. As such, the trial bodies and implants can be employed without utilization of external distraction or distraction maintained in another disc space location during trial instrument and implant insertion. However, secondary distraction can be used to at least partially maintain disc space distraction upon withdrawal of the implants and trial bodies can be employed. For example, pedicle screws and a rod can be employed on the contralateral side to at least partially maintain distraction obtained with a particular implant or trial instrument; however, use of the same is not required. Further, the trial bodies provide an indication of the fit of the implant into the disc space location. Since the implant may include a shape that corresponds to that of the trial instrument, there is an immediate confirmation to the surgeon that the corresponding implant will fit into the space occupied by the trial instrument.

The trial bodies and/or implants are then sequentially inserted and, if necessary, withdrawn through the annulus opening and into the disc space. Since the implants are self-distracting, it is not necessary to chisel, drill or otherwise form the vertebral endplates to receive the implant, although such steps are not precluded. Consequently, fewer steps in the surgical procedure are necessary since requirements for bilateral distraction, external distraction, chiseling, drilling and reaming are eliminated. In addition, the lack of other instruments or devices in the disc space facilitates visualization of the disc space preparation, trial instrument insertion, and/or implant insertion. Elimination of cutting instruments in the disc space also may improve the safety of the procedure.

Minimally invasive techniques employing the trial instruments and implants are contemplated. In any particular patient, the implants can be inserted via any one or combination of posterior, postero-lateral, antero-lateral, transforaminal, far lateral and/or anterior approaches. Implant insertion can occur through a single pathway to a collapsed spinal disc space, or through multiple pathways to the collapsed disc space, or through multiple pathways to multiple levels of collapsed discs of the spinal column. Since the implant, and trial instruments if employed, are inserted into the same disc space location from the same approach, the entire procedure for inserting an implant can be completed through one pathway. If a multiple pathway procedure is to be employed, the surgeon can complete implant insertion through one pathway before creating and moving to work in a second pathway.

Since distraction and implant insertion occur along the same pathway to the collapsed disc space, the implants and trial instruments are suited for use in minimally invasive procedures which employ a retractor sleeve to provide a pathway to the collapsed disc space. Such retractor sleeves can employ any one or combination of an endoscopic viewing element in the working channel, a microscopic viewing system over the proximal end of the retractor sleeve, fluoroscopic viewing, loupes, naked eye and/or image guidance.

In accordance with certain method embodiments, an implant is inserted between the vertebral bodies. Any of the implant embodiments described above, as well as certain other implants, may be inserted as part of the methods described herein. The implants of some embodiments may be impacted or pushed into the disc space. As a result, disruption to the annulus tissue and tissue approaching the collapsed disc space is reduced since the footprint of the implant in the disc space can be the same as the footprint occupied in the implant's approach to the disc space. Also, by providing the implant with the same footprint as the trial instrument, and by performing distraction and implant insertion through the same portal or pathway, no additional tissue dissection and/or retraction is required to accommodate distraction of the disc space during implant insertion.

With reference to FIG. 33, an anteriorly placed implant 1 with an at least partially curved anterior wall 10 is illustrated. In some embodiments, the act of inserting the implant 1 includes placing the implant 1 anteriorly between vertebral bodies such that the first curved portion 10a and the second curved portion 10b of the anterior sidewall 10 are substantially located between a cortical rim of the upper vertebra and the cortical rim 610 of the lower vertebra. In some embodiments, the first curved portion 10a and the second curved portion 10b may one or both be located between cortical rims of the upper and lower vertebrae. In other embodiments, the entire anterior wall 10 may be located between cortical rims of the upper and lower vertebrae. The disclosed curvatures of the anterior sidewall 10 may useful to permit the implant 1, and particularly first and second curved portions 10a, 10b, to be substantially located between the cortical rims of the supported vertebrae without extending beyond the bounds of the cortical rims. The cortical rim 610 provides more support than the interior, cancellous bone 620 of the vertebral body V.

Also contemplated is a method for inserting an intervertebral implant that includes means for accessing a collapsed spinal disc space. A number of trial bodies are provided with leading end portions sized for insertion into a non-distracted disc space. The trial bodies are sequentially inserted into and removed from the disc space. The trial instrument providing the desired disc space height is used to select an implant having a height and a self-distracting leading end portion corresponding to the height and leading end portion of the last inserted trial instrument. The implant is then inserted into the non-distracted disc space to restore the disc space and postoperatively maintain the desired disc space height.

While embodiments of the invention have been illustrated and described in detail in the disclosure, the disclosure is to be considered as illustrative and not restrictive in character, and that all changes and modifications that come within the spirit of the invention are desired to be protected.

What is claimed is:

1. An implant positionable in a spinal disc space between an upper vertebra and a lower vertebra, comprising:
    a leading end portion, an opposite trailing end portion, and a longitudinal axis extending between the leading and trailing end portions;
    a convexly curved upper surface orientable toward the upper vertebra;
    a convexly curved lower surface orientable toward the lower vertebra;
    an anterior sidewall extending between the leading end portion and the trailing end portion, the anterior sidewall including a maximally anterior portion defining a maximum width of the implant, a first anteriorly-facing convexly curved surface portion defining a first convex curve extending from the leading end portion to the maximally anterior portion, and a second anteriorly-facing convexly curved surface portion defining a second convex curve extending from the trailing end portion to the maximally anterior portion; and
    a posterior sidewall arranged opposite the anterior sidewall and extending between the leading end portion and the trailing end portion.

2. The implant of claim 1 wherein the convexly curved upper surface and the convexly curved lower surface are each convexly curved along an entire length of the implant from the leading end portion to the trailing end portion.

3. The implant of claim 1 wherein the convexly curved upper surface and the convexly curved lower surface are each curved along a constant radius of curvature.

4. The implant of claim 1 wherein the first anteriorly-facing convexly curved surface portion is symmetrical to the second anteriorly-facing convexly curved surface portion relative to the maximally anterior portion.

5. The implant of claim 1 wherein the first and second convex curves defined by the first and second anteriorly-facing convexly curved surface portions are part of the same convex curvature, and wherein the maximally anterior portion comprises a point along the convex curvature.

6. The implant of claim 1 wherein the implant defines a cavity extending therethrough from the convexly curved upper surface to the convexly curved lower surface.

7. The implant of claim 6 wherein the anterior and posterior sidewalls each define an opening in communication with the cavity.

8. The implant of claim 6 further comprising a bone growth material positioned within the cavity.

9. The implant of claim 1 wherein the convexly curved upper and lower surfaces each include a number of engagement members positioned along portions of the anterior and posterior sidewalls and projecting outwardly therefrom for engagement with bony tissue.

10. The implant of claim 9 wherein the engagement members comprise a plurality of teeth.

11. The implant of claim 1 wherein the implant defines a varying implant height between the convexly curved upper and lower surfaces, the varying implant height being generally symmetrical relative to a transverse axis passing through a location of the implant defining a maximum implant height.

12. The implant of claim 11 wherein the convexly curved upper and lower surfaces each extend along a constant radius of curvature.

13. The implant of claim 1 wherein the convexly curved upper and lower surfaces each include convex surface portions arranged on opposite sides of a transverse axis passing through a location of the implant defining a maximum implant height, and wherein the convex surface portions are symmetrical relative to the transverse axis.

14. The implant of claim 13 wherein the convex surface portions extend commonly along a constant radius of curvature.

15. The implant of claim 1 wherein the convexly curved upper and lower surfaces each include convex surface portions arranged on opposite sides of a transverse axis passing through a location of the implant defining a maximum implant height, and wherein the convex surface portions extend commonly along a constant radius of curvature.

16. The implant of claim 1 wherein the leading end portion includes a convexly curved leading end surface defining a convex curvature extending from the convexly curved upper surface to the convexly curved lower surface.

17. An implant positionable in a spinal disc space between an upper vertebra and a lower vertebra, comprising:
 a leading end portion, an opposite trailing end portion, and a longitudinal axis extending between the leading and trailing end portions;
 a convexly curved upper surface orientable toward the upper vertebra;
 a convexly curved lower surface orientable toward the lower vertebra;
 an anterior sidewall extending between the leading end portion and the trailing end portion, the anterior sidewall including a maximally anterior portion defining a maximum width of the implant, a first anteriorly-facing convexly curved surface portion defining a first convex curve extending from the leading end portion to the maximally anterior portion, and a second anteriorly-facing convexly curved surface portion defining a second convex curve extending from the trailing end portion to the maximally anterior portion; and
 a posterior sidewall arranged opposite the anterior sidewall and extending between the leading end portion and the trailing end portion; and
 wherein the leading end portion includes a self-distracting nose defining a first convex curvature that curves along the height of the implant from the convexly curved upper surface to a leading end surface, the nose also defining a second convex curvature that curves along the height of the implant from the convexly curved lower surface to the leading end surface.

18. The implant of claim 17 wherein the self-distracting nose defines a third convex curvature extending from the anterior sidewall to the posterior sidewall.

19. An implant positionable in a spinal disc space between an upper vertebra and a lower vertebra, comprising:
 a leading end portion, an opposite trailing end portion, and a longitudinal axis extending between the leading and trailing end portions;
 a convexly curved upper surface orientable toward the upper vertebra;
 a convexly curved lower surface orientable toward the lower vertebra;
 an anterior sidewall extending between the leading end portion and the trailing end portion, the anterior sidewall including a maximally anterior portion defining a maximum width of the implant, a first anteriorly-facing convexly curved surface portion defining a first convex curve extending from the leading end portion to the maximally anterior portion, and a second anteriorly-facing convexly curved surface portion defining a second convex curve extending from the trailing end portion to the maximally anterior portion; and
 a posterior sidewall arranged opposite the anterior sidewall and extending between the leading end portion and the trailing end portion;
 a first notch in the anterior sidewall and extending to the trailing end portion; and
 a second notch in the posterior sidewall and extending to the trailing end portion.

20. The implant of claim 19 further comprising a coupling member having first and second fingers positionable in respective ones of the first and second notches to secure the implant to the coupling member.

* * * * *